United States Patent
Sakata et al.

(10) Patent No.: US 7,361,653 B2
(45) Date of Patent: Apr. 22, 2008

(54) PEST CONTROL AGENT COMPOSITION AND METHOD OF USING THE SAME

(75) Inventors: Kazuyuki Sakata, Kawachinagano (JP); Masayuki Morimoto, Kawachinagano (JP); Hiroshi Kodama, Hashimoto (JP); Tetsuyosi Nishimatsu, Kawachinagano (JP)

(73) Assignee: Nihon Nohyaku Co., Ltd, Tokyo (JP)

( * ) Notice: Subject to any disclaimer, the term of this patent is extended or adjusted under 35 U.S.C. 154(b) by 554 days.

(21) Appl. No.: 10/475,030

(22) PCT Filed: Apr. 16, 2002

(86) PCT No.: PCT/JP02/03780

§ 371 (c)(1),
(2), (4) Date: Oct. 16, 2003

(87) PCT Pub. No.: WO02/087334

PCT Pub. Date: Nov. 7, 2002

(65) Prior Publication Data

US 2004/0077500 A1    Apr. 22, 2004

(30) Foreign Application Priority Data

Apr. 17, 2001 (JP) .............................. 2001-118840
Apr. 26, 2001 (JP) .............................. 2001-129588

(51) Int. Cl.
*A01N 43/88* (2006.01)
*A01N 37/18* (2006.01)
*A01N 37/22* (2006.01)
*A01N 37/24* (2006.01)
*A01N 37/26* (2006.01)
*A01N 37/28* (2006.01)
*A01N 37/30* (2006.01)

(52) U.S. Cl. ................... 514/223.8; 514/617; 514/618; 514/619; 514/621; 514/622

(58) Field of Classification Search ............... 514/223.8
See application file for complete search history.

(56) References Cited

U.S. PATENT DOCUMENTS

| | | | |
|---|---|---|---|
| 4,694,016 A | * | 9/1987 | Lu et al. ..................... 514/380 |
| 5,646,157 A | * | 7/1997 | Hohl ........................... 514/272 |
| 6,603,044 B1 | * | 8/2003 | Tohnishi et al. ............ 564/154 |
| 6,642,379 B1 | * | 11/2003 | Furuya et al. ................. 544/88 |
| 6,864,289 B1 | * | 3/2005 | Tohnishi et al. ............ 514/617 |
| 7,256,192 B2 | * | 8/2007 | Tohnishi et al. ............ 514/247 |
| 2004/0063738 A1 | * | 4/2004 | Lahm et al. ................. 514/275 |

FOREIGN PATENT DOCUMENTS

| | | | |
|---|---|---|---|
| EP | 919542 | * | 6/1999 |
| EP | 1006107 A2 | * | 6/2000 |
| JP | 2001-064268 | * | 3/2001 |
| JP | 2001-131141 | * | 5/2001 |
| JP | 2001-158764 | * | 6/2001 |
| JP | 2001-240580 | * | 9/2001 |

* cited by examiner

*Primary Examiner*—John Pak
(74) *Attorney, Agent, or Firm*—Manelli, Denison & Selter; Paul E. White

(57) ABSTRACT

The present invention relates to a composition for noxious organisms-controlling agent having a synergistic effect and a method for using said composition, which comprises, as active ingredients thereof, one or more compounds selected from the phthalamide derivatives represented by general formula (I) being useful as an insecticide or acaricide and one or more compounds selected from the compounds having insecticidal, acaricidal or nematocidal activity:

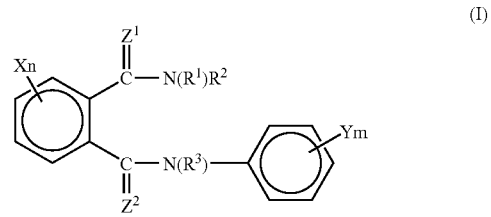

(I)

wherein $R^1$, $R^2$ and $R^3$ may be the same or different and each represent hydrogen atom, $C_3$-$C_6$ cycloalkyl, $-A^1$-Qp, etc., each of X and Y may be the same or different and represents hydrogen atom, halogen atom, etc., n is an integer of 1 to 4, m is an integer of 1 to 5, and each of $Z_1$ and $Z_2$ represents O or S.

4 Claims, No Drawings

PEST CONTROL AGENT COMPOSITION AND METHOD OF USING THE SAME

This application is the national phase of international application PCT/JP02/03780 filed 16 Apr. 2002 which designated the U.S.

TECHNICAL FIELD

The present invention relates to a composition for noxious organisms-controlling agent having a synergistic effect and a method for using said composition, which comprises a phthalamide derivative represented by general formula (I) being useful as an insecticide or acaricide and one or more compounds selected from the compounds having insecticidal, acaricidal or nematocidal activity.

BACKGROUND ART

The phthalamide derivatives of the present invention represented by general formula (I) are known compounds disclosed in JP-A-11-240857 and JP-A-2001-131141, wherein it is mentioned that these compounds have an insecticidal or acaricidal activity.

On the other hand, the compounds having insecticidal, acaricidal or nematocidal activity, as the second active ingredient of the present invention, are known compounds as disclosed in The Pesticide Manual Eleventh Edition 1997, etc.

DISCLOSURE OF THE INVENTION

There exist many noxious organisms which are difficult or impossible to control by the use of a single member selected from the phthalamide derivatives represented by the general formula (I) of the present invention and the insecticidal, acaricidal or nematocidal compounds. Accordingly, it is expected that discovery of the means and method for the effective control of such noxious organisms will lead to a more effective production of crop plants.

With the aim of solving the problem mentioned above, the present inventors have conducted extensive studies. As a result, it has been found that a plurality of noxious organisms can be controlled effectively by the combined use of one or more compounds selected from the phthalamide derivatives represented by the general formula (I) and one or more compounds selected from the insecticidal, acaricidal or nematocidal compounds. The present invention has been accomplished on the basis of this finding.

The present invention relates to a composition for noxious organisms-controlling agent comprising, as active ingredients thereof, one or more compounds selected from the phthalamide derivatives represented by the general formula (I):

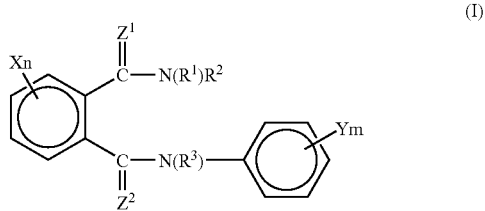
(I)

wherein $R^1$, $R^2$ and $R^3$, which may be the same or different, each represent a hydrogen atom, a $C_3$-$C_6$ cycloalkyl group, a halo $C_3$-$C_6$ cycloalkyl group or -$A^1$-$Q_p$ (in this formula, $A^1$ represents a $C_1$-$C_8$ alkylene group, a $C_3$-$C_6$ alkenylene group or a $C_3$-$C_6$ alkynylene group; Q represents a hydrogen atom; a halogen atom; a cyano group; a nitro group; a halo $C_1$-$C_6$ alkyl group; a $C_3$-$C_6$ cycloalkyl group; a halo $C_3$-$C_6$ cycloalkyl group; a $C_1$-$C_6$ alkoxycarbonyl group; a di $C_1$-$C_6$ alkoxyphosphoryl group in which the alkoxy groups may be the same or different; a di $C_1$-$C_6$ alkoxythiophosphoryl group in which the alkoxy groups may be the same or different; a diphenylphosphino group; a diphenylphosphono group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group means a pyridyl group, a pyridine-N-oxide group, a pyrimidinyl group, a furyl group, a tetrahydrofuryl group, a thienyl group, a tetrahydrothienyl group, a tetrahydropyranyl group, a tetrahydrothiopyranyl group, an oxazolyl group, an isoxazolyl group, an oxadiazolyl group, a thiazolyl group, an isothiazolyl group, a thiadiazolyl group, an imidazolyl group, a triazolyl group or a pyrazolyl group); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$Z^3$-$R^4$ (in this formula, $Z^3$ represents —O—, —S—, —SO—, —SO$_2$— or —N($R^5$)— (in this formula, $R^5$ represents a hydrogen atom; a $C_1$-$C_6$ alkylcarbonyl group; a halo $C_1$-$C_6$ alkylcarbonyl group; a $C_1$-$C_6$ alkoxycarbonyl group; a phenylcarbonyl group; a substituted phenylcarbonyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkoxycarbonyl group; or a substituted phenyl $C_1$-$C_4$ alkoxycarbonyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group), and $R^4$ represents a hydrogen atom; a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ alkynyl group; a halo $C_3$-$C_6$ alkynyl group; a $C_3$-$C_6$ cycloalkyl group; a halo $C_3$-$C_6$ cycloalkyl group; a $C_1$-$C_6$ alkylcarbonyl group; a halo $C_1$-$C_6$ alkylcarbonyl group; a $C_1$-$C_6$ alkoxycarbonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); or a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group); and p represents an integer of 1-4); and $R^1$ and $R^2$ may be taken conjointly to form a 4- to 7-membered ring which may be interrupted by one to three, the same or different hetero atoms selected from oxygen atom, sulfur atom and nitrogen atom;

X may be the same or different and represents a hydrogen atom; a halogen atom; a cyano group; a nitro group; a $C_3$-$C_6$ cycloalkyl group; a halo $C_3$-$C_6$ cycloalkyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^2$-$R^6$ (in this formula, $A^2$ represents —O—, —S—, —SO—, —SO$_2$—, —C(=O)—, —C(=NOR$^7$)— (in this formula, $R^7$ represents a hydrogen atom, a $C_1$-$C_6$ alkyl group, a halo $C_1$-$C_6$ alkyl group, a $C_3$-$C_6$ alkenyl group, a halo $C_3$-$C_6$ alkenyl group, a $C_3$-$C_6$ alkynyl group, a cyclo $C_3$-$C_6$ alkyl group, a phenyl $C_1$-$C_4$ alkyl group or a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group), a $C_1$-$C_6$ alkylene group, a halo $C_1$-$C_6$ alkylene group, a $C_2$-$C_6$ alkenylene group, a halo $C_2$-$C_6$ alkenylene group, a $C_2$-$C_6$ alkynylene group or a halo $C_3$-$C_6$ alkynylene group, and (1) in a case where $A^2$ represents —O—, —S—, —SO— or —SO$_2$—, $R^6$ represents a halo $C_3$-$C_6$ cycloalkyl group; a halo $C_3$-$C_6$ cycloalkenyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^3$-$R^8$ (in this formula, $A^3$ represents a $C_1$-$C_6$ alkylene group, a halo $C_1$-$C_6$ alkylene group, a $C_3$-$C_6$ alkenylene group, a halo $C_3$-$C_6$ alkenylene group, a $C_3$-$C_6$ alkynylene group or a halo $C_3$-$C_6$ alkynylene group, and $R^8$ represents a hydrogen atom; a halogen atom; a $C_3$-$C_6$ cycloalkyl group; a halo $C_3$-$C_6$ cycloalkyl group; a $C_1$-$C_6$ alkoxycarbonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^4$-$R^9$ (in this formula, $A^4$ represents —O—, —S—, —SO—, —SO$_2$— or —C(=O), and $R^9$ represents a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ cycloalkyl group; a halo $C_3$-$C_6$ cycloalkyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); or a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group)), (2) in a case where $A^2$ represents —C(=O)— or —C(=NOR$^7$)— (in this formula, $R^7$ is as defined above), $R^6$ represents a $C_1$-$C_6$ alkyl group; a halo $C_1$-$C_6$ alkyl group; a $C_2$-$C_6$ alkenyl group; a halo $C_2$-$C_6$ alkenyl group; a $C_3$-$C_6$ cycloalkyl group; a halo $C_3$-$C_6$ cycloalkyl group; a $C_1$-$C_6$ alkoxy group; a $C_1$-$C_6$ alkylthio group; a mono $C_1$-$C_6$ alkylamino group; a di $C_1$-$C_6$ alkylamino group in which the alkyl groups may be the same or different; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenylamino group; a substituted phenylamino group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); or a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group, and (3) in a case where $A^2$ represents a $C_1$-$C_6$ alkylene group, a halo $C_1$-$C_6$ alkylene group, a $C_2$-$C_6$ alkenylene group, a halo $C_2$-$C_6$ alkenylene group, a $C_2$-$C_6$ alkynylene group or a halo $C_3$-$C_6$ alkynylene group, $R^6$ represents a hydrogen atom; a halogen atom; a $C_3$-$C_6$ cycloalkyl group; a halo $C_3$-$C_6$ cycloalkyl group; a $C_1$-$C_6$ alkoxycarbonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^5$-$R^{10}$ (in this formula, $A^5$ represents —O—, —S—, —SO— or —$SO_2$—, and $R^{10}$ represents a $C_3$-$C_6$ cycloalkyl group; a halo $C_3$-$C_6$ cycloalkyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^6$-$R^{11}$ (in this formula, $A^6$ represents a $C_1$-$C_6$ alkylene group; a halo $C_1$-$C_6$ alkylene group; a $C_2$-$C_6$ alkenylene group; a halo $C_2$-$C_6$ alkenylene group; a $C_2$-$C_6$ alkynylene group; or a halo $C_3$-$C_6$ alkynylene group; and $R^{11}$ represents a hydrogen atom; a halogen atom; a $C_3$-$C_6$ cycloalkyl group; a halo $C_3$-$C_6$ cycloalkyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenylthio group; a substituted phenylthio group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above; or a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group))), and n represents an integer of 1-4; and X may be taken conjointly together with an adjacent carbon atom on the phenyl ring to form a condensed ring (the term condensed ring means naphthalene, tetrahydronaphthalene, indene, indane, quinoline, quinazoline, chromane, isochromane, indole, indoline, benzodioxane, benzodioxole, benzofuran, dihydrobenzofuran, benzothiophene, dihydrobenzothiophene, benzoxazole, benzothiazole, benzimidazole or indazole), and said condensed ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, phenyl group, substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group, heterocyclic group (the term heterocyclic group is as defined above) and substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and Y may be the same or different and represents a hydrogen atom; a halogen atom; a cyano group; a nitro group; a halo $C_3$-$C_6$ cycloalkyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group (the term heterocyclic group is as defined above); a substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^2$-$R^6$ (in this formula, $A^2$ and $R^6$ are as defined above); and m represents an integer of 1-5; and Y may be taken conjointly together with an adjacent carbon atom on the phenyl ring to form a condensed ring (the term condensed ring is as defined above), and said condensed ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, phenyl group, substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group, heterocyclic group (the term heterocyclic group is as defined above) and substituted heterocyclic group (the term heterocyclic group is as defined above) having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and $Z^1$ and $Z^2$ represent an oxygen atom or a sulfur atom; and
one or more compounds selected from compounds having an insecticidal, acaricidal or nematocidal activity;
and to a method for using said composition.

The noxious organisms-controlling agent of the present invention exhibits a marked effect even when dosage thereof is so low that any of the ingredients constituting said agent can exhibit no effect at such a low dosage if used singly, and exhibits a marked controlling effect against noxious organisms and agent-resistant noxious organisms which cannot be controlled with any of the single ingredients.

MODE FOR PRACTICE OF THE INVENTION

In the definition of general formula (I) representing the phthalamide derivative of this invention, the term "halogen atom" means chlorine atom, bromine atom, iodine atom or fluorine atom; "$C_1$-$C_6$ alkyl" means a straight or branched chain alkyl group having 1-6 carbon atoms such as methyl, ethyl, n-propyl, i-propyl, n-butyl, i-butyl, s-butyl, t-butyl, n-pentyl, n-hexyl and the like; "halo $C_1$-$C_6$ alkyl" means a straight or branched chain alkyl group having 1-6 carbon atoms which is substituted with at least one, the same or different halogen atoms; "$C_1$-$C_8$ alkylene" means a straight or branched chain alkylene group having 1-8 carbon atoms such as methylene, ethylene, propylene, trimethylene, dimethylmethylene, tetramethylene, isobutylene, dimethylethylene, octamethylene and the like;

As the "4- to 7-membered ring which may be interrupted by 1 to 3, the same or different hetero atoms selected from oxygen atom, sulfur atom and nitrogen atom" formed through a mutual combination of $R^1$ and $R^2$, for example, azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring, dithiazine ring and the like can be referred to.

In some cases, the phthalamide derivative of the present invention represented by general formula (I) may have an asymmetric carbon atom or an asymmetric center in the structural formula thereof, and may have two or more optical isomers. The present invention involves all such optical isomers and mixtures consisting of the optical isomers at arbitrary ratios. In some cases, the present invention involves salts, hydrates and the like of these compounds.

The phthalamide derivatives represented by general formula (I) can be obtained by using the compounds and production processes disclosed in JP-A-11-240857 and JP-A-2001-131141.

Among the compounds represented by general formula (I), preferable are those in which $R^1$ represents a hydrogen atom, $R^2$ represents a $C_1$-$C_6$ alkyl group, a $C_1$-$C_6$ alkylthio $C_1$-$C_6$ alkyl group, a $C_1$-$C_6$ alkylsulfinyl $C_1$-$C_6$ alkyl group or a $C_1$-$C_6$ alkylsulfonyl $C_1$-$C_6$ alkyl group, $R^3$ represents a hydrogen atom, X represents a halogen atom, n represents 1, $Z^1$ and $Z^2$ represent an oxygen atom, Y which may be the same or different represents a halogen atom, a $C_1$-$C_6$ alkyl group, a halo $C_1$-$C_6$ alkyl group or a halo $C_1$-$C_6$ alkoxy group, and m represents 2 or 3. Among these compounds, particularly preferable are the following compounds: $N^2$-(1,1-dimethyl-2-methylthioethyl)-3-iodo-$N^1$-{2-methyl-4-[1,2,2,2-tetrafluoro-1-(trifluoromethyl)ethyl]phenyl}-phthalamide, $N^2$-(1,1-dimethyl-2-methylsulfonylethyl)-3-iodo-$N^1$-{2-methyl-4-[(1,2,2,2-tetrafluoro-1-(trifluoromethyl)ethyl]-phenyl}phthalamide and $N^2$-(1,1-dimethyl-2-methylsulfinylethyl)-3-iodo-$N^1$-{2-methyl-4-[1,2,2,2-tetrafluoro-1-(trifluoromethyl)ethyl]-phenyl}phthalamide.

In Table 1, typical compounds of the present invention are listed. This invention, however, is by no means limited by these compounds. As examples of such compounds, the compounds disclosed in JP-A-11-240857 and JP-A-2001-131141 can be referred to.

General Formula (I)

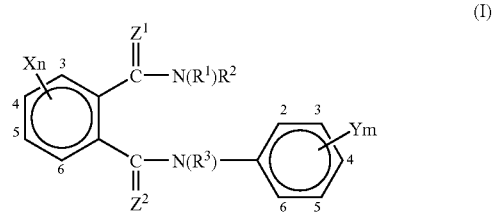

TABLE 1

($Z^1$=$Z^2$=O)

| No | $R^1$ | $R^2$ | $R^3$ | Xn | Ym | Property mp° C. |
|---|---|---|---|---|---|---|
| 1 | $CH_3$ | H | H | 3-$NO_2$ | 2-$CH_3$-5-Cl | 169-171 |
| 2 | $C_2H_5$ | H | H | 3-Cl | 2-$CH_3$-4-$OCHF_2$ | 179-180 |
| 3 | $C_2H_5$ | H | H | 3-$NO_2$ | 2-$CH_3$-5-Cl | 175-177 |
| 4 | n-$C_3H_7$ | H | H | 3-$NO_2$ | 2-$CH_3$-4-$OCHF_2$ | 184-186 |
| 5 | i-$C_3H_7$ | H | H | 3-Cl | 4-$C_4H_9$-n | 169-171 |
| 6 | i-$C_3H_7$ | H | H | 3-Cl | 4-$C_4H_9$-t | 224-226 |
| 7 | i-$C_3H_7$ | H | H | 3-Cl | 4-$CF(CF_3)_2$ | 198-200 |
| 8 | i-$C_3H_7$ | H | H | 3-Cl | 4-$CF_2CF_2CF_3$ | 203-204 |
| 9 | i-$C_3H_7$ | H | H | 3-Cl | 4-$(CF_2)_3CF_3$ | 176-178 |
| 10 | i-$C_3H_7$ | H | H | 3-Cl | 4-$OCF_2CHFOC_3F_7$-n | 169-171 |
| 11 | i-$C_3H_7$ | H | H | 6-Cl | 4-$SCH_3$ | 193-195 |
| 12 | i-$C_3H_7$ | H | H | 3-Cl | 4-$SO_2CH_3$ | 208-210 |
| 13 | i-$C_3H_7$ | H | H | 3-Cl | 4-$SCHF_2$ | 220-222 |
| 14 | i-$C_3H_7$ | H | H | 3-Cl | 4-$SCF_2CHF_2$ | 198-200 |
| 15 | i-$C_3H_7$ | H | H | 3-Cl | 4-$SO_2CF_2CHF_2$ | 227-230 |
| 16 | i-$C_3H_7$ | H | H | 3-Cl | 4-$COCH_3$ | 217-219 |
| 17 | i-$C_3H_7$ | H | H | 3-Cl | 4-Ph | 215-217 |
| 18 | i-$C_3H_7$ | H | H | 3-Cl | 2-$CH_3$-4-$OCH_3$ | 191-192 |
| 19 | i-$C_3H_7$ | H | H | 3-Cl | 2-$CH_3$-4-$CF_2CF_3$ | 199-200 |
| 20 | i-$C_3H_7$ | H | H | 3-Cl | 2-$CH_3$-4-$OCF_3$ | 199-201 |
| 21 | i-$C_3H_7$ | H | H | 3,6-$Cl_2$ | 2-$CH_3$-4-$OCHF_2$ | 221-222 |
| 22 | i-$C_3H_7$ | H | H | 3-Br | 4-$OCF_3$ | 208-210 |
| 23 | i-$C_3H_7$ | H | H | 3-Br | 2-$CH_3$-4-$CF_2CF_3$ | 201-202 |
| 24 | i-$C_3H_7$ | H | H | 3-Br | 2-$CH_3$-4-$CF(CF_3)_2$ | 222-224 |
| 25 | i-$C_3H_7$ | H | H | 3-Br | 2-$CH_3$-4-$SCH_3$ | 215-217 |
| 26 | i-$C_3H_7$ | H | H | 3-Br | 2-$CH_3$-4-(3-$CF_3$-PhO) | 156-158 |
| 27 | i-$C_3H_7$ | H | H | 3-Br | 2-$CH_3$-4-(5-$CF_3$-2-Pyi—O) | 182-184 |
| 28 | i-$C_3H_7$ | H | H | 3-Br | -3-$OCH_2O$-4- | 195-198 |
| 29 | i-$C_3H_7$ | H | H | 6-Br | 2-$CH_3$-4-$OCF_2CHFCF_3$ | 212-213 |
| 30 | i-$C_3H_7$ | H | H | 6-Br | 2-$CH_3$-4-$OCF_2CHClF$ | 211-213 |
| 31 | i-$C_3H_7$ | H | H | 6-Br | 2-$CH_3$-4-$OCF_2CHF_2$ | 214-215 |
| 32 | i-$C_3H_7$ | H | H | 5,6-$Br_2$ | 2-$CH_3$-4-$OCHF_2$ | 208-210 |
| 33 | i-$C_3H_7$ | H | H | 3-I | 4-$CF_2CF_2CF_3$ | 217-219 |
| 34 | i-$C_3H_7$ | H | H | 3-I | 4-$CF(CF_3)_2$ | 209-211 |
| 35 | i-$C_3H_7$ | H | H | 3-I | 4-$SCH_2CHF_2$ | 195-197 |
| 36 | i-$C_3H_7$ | H | H | 3-I | 4-$SCHF_2$ | 204-206 |
| 37 | i-$C_3H_7$ | H | H | 3-I | 4-$S(CF_2)_3CF_3$ | 185-187 |
| 38 | i-$C_3H_7$ | H | H | 3-I | 2-$CH_3$-4-Cl | 215-217 |
| 39 | i-$C_3H_7$ | H | H | 3-I | 2-Cl-4-$CF_3$ | 170-171 |
| 40 | i-$C_3H_7$ | H | H | 3-I | 2-$CH_3$-4-$CF_3$ | 202-203 |
| 41 | i-$C_3H_7$ | H | H | 3-I | 2-$CH_3$-4-$CF_2CF_3$ | 195-196 |
| 42 | i-$C_3H_7$ | H | H | 3-I | 2-$CH_3$-4-$CF_2CF_2CF_3$ | 193-195 |
| 43 | i-$C_3H_7$ | H | H | 3-I | 2-$CH_3$-4-$CF(CF_3)_2$ | 211-213 |
| 44 | i-$C_3H_7$ | H | H | 3-I | 2-$CH_3$-4-$OCF_3$ | 214-216 |
| 45 | i-$C_3H_7$ | H | H | 3-I | 2-$CH_3$-4-$OCHF_2$ | 207-209 |
| 46 | i-$C_3H_7$ | H | H | 3-I | 2-$CH_3$-4-$OCH_2CF_2CHF_2$ | 229-231 |
| 47 | i-$C_3H_7$ | H | H | 3-I | 2-$CH_3$-4-$OCF_2CHFCF_3$ | 213-214 |
| 48 | i-$C_3H_7$ | H | H | 3-I | 2-Cl-4-$OCF_3$ | 173-175 |
| 49 | i-$C_3H_7$ | H | H | 6-I | 4-$SCF(CF_3)_2$ | 216-218 |
| 50 | i-$C_3H_7$ | H | H | 6-I | 2-Cl-4-$CF_3$ | 195-196 |
| 51 | i-$C_3H_7$ | H | H | 6-I | 2-$CH_3$-4-$CF(CF_3)_2$ | 237-239 |
| 52 | i-$C_3H_7$ | H | H | 6-I | 2-Cl-4-$CF_2CF_2CF_3$ | 199-200 |
| 53 | i-$C_3H_7$ | H | H | 3-F | 2-$CH_3$-4-$CF(CF_3)_2$ | 241-243 |
| 54 | i-$C_3H_7$ | H | H | 3-F | 2-$CH_3$-4-$OCF_3$ | 183-184 |
| 55 | i-$C_3H_7$ | H | H | 3-$NO_2$ | 3-F | 228-230 |
| 56 | i-$C_3H_7$ | H | H | 3-$NO_2$ | 2-$CH_3$-4-$OCHF_2$ | 186-188 |
| 57 | n-$C_4H_9$ | H | H | 3-$NO_2$ | 2-$CH_3$-5-Cl | 172-174 |
| 58 | s-$C_4H_9$ | H | H | 6-Cl | 2-$CH_3$-4-$OCHF_2$ | 213-215 |
| 59 | t-$C_4H_9$ | H | H | 3-$NO_2$ | 2-$CH_3$-4-$OCHF_2$ | 172-173 |
| 60 | c-$C_3H_5$ | H | H | 3-Cl | 2-$CH_3$-4-$OCHF_2$ | 156-158 |
| 61 | c-$C_4H_7$ | H | H | 3-$NO_2$ | 2-$CH_3$-5-Cl | 206-208 |
| 62 | c-$C_5H_9$ | H | H | 3-$NO_2$ | 2-$CH_3$-5-Cl | 200-202 |
| 63 | c-$C_6H_{11}$ | H | H | 3-$NO_2$ | 2-$CH_3$-5-Cl | 225-227 |
| 64 | $CH_2C_3H_5$-c | H | H | 3-$NO_2$ | 2-$CH_3$-5-F | 190-192 |
| 65 | $CH_2CH_2Cl$ | H | H | 3-$NO_2$ | 2-$CH_3$-5-F | 179-181 |
| 66 | $CH_2CH=CH_2$ | H | H | 3-$NO_2$ | 2-$CH_3$-4-$OCHF_2$ | 194-195 |
| 67 | $CH_2C\equiv CH$ | H | H | 3-$NO_2$ | 2-$CH_3$-4-$OCHF_2$ | 190-191 |
| 68 | i-$C_3H_7$ | H | H | 3-Cl | 4-$CH=CBr_2$ | 209.8-214.8 |
| 69 | i-$C_3H_7$ | H | H | 6-Cl | 4-$CH=CCl_2$ | 199.7 |
| 70 | i-$C_3H_7$ | H | H | 3-I | 4-$CH=C(Cl)CF_3$ | 196.6 |
| 71 | i-$C_3H_7$ | H | H | 6-I | 4-$CH=C(Cl)CF_3$ | 203.3 |
| 72 | t-$C_4H_9$ | H | H | 3-I | 2-$CH_3$-4-$CF_2CF_3$ | 205-207 |

TABLE 1-continued ($Z^1=Z^2=O$)

| No | $R^1$ | $R^2$ | $R^3$ | Xn | Ym | Property mp° C. |
|---|---|---|---|---|---|---|
| 73 | t-$C_4H_9$ | H | H | 6-I | 2-$CH_3$-4-$CF_2CF_3$ | 216-217 |
| 74 | n-$C_4H_9$ | H | H | 6-I | 2-$CH_3$-4-$CF_2CF_3$ | 181.8-187.7 |
| 75 | n-$C_5H_{11}$ | H | H | 6-I | 2-$CH_3$-4-$CF_2CF_3$ | 168.7-171.3 |
| 76 | i-$C_3H_7$ | H | H | 6-$CH_3$ | 2-$CH_3$-4-$CF_2CF_3$ | 177-179 |
| 77 | $CH_2CH_2OC_2H_5$ | H | H | 3-I | 2-$CH_3$-4-$CF_2CF_3$ | 146.5-150.3 |
| 78 | $CH_2CH_2OC_2H_5$ | H | H | 6-I | 2-$CH_3$-4-$CF_2CF_3$ | 157.3-160.4 |
| 79 | c-$C_5H_9$ | H | H | 6-I | 2-$CH_3$-4-$CF_2CF_3$ | 205.2 |
| 80 | c-$C_6H_{11}$ | H | H | 6-I | 2-$CH_3$-4-$CF_2CF_3$ | 239.0-244.4 |
| 81 | i-$C_3H_7$ | H | H | 3-I | 4-$SCF_3$ | 226-227 |
| 82 | i-$C_3H_7$ | H | H | 3-$NO_2$ | 4-$SOCF_3$ | 202-205 |
| 83 | i-$C_3H_7$ | H | H | 3-Cl | 4-$SOCF_3$ | 242-244 |
| 84 | i-$C_4H_9$ | H | H | 3-I | 2-$CH_3$-4-$CF_2CF_3$ | 200.4-206.8 |
| 85 | s-$C_4H_9$ | H | H | 6-I | 2-$CH_3$-4-$CF_2CF_3$ | 216.1-218.0 |
| 86 | $CH(C_2H_5)$—$CH_2OCH_3$ | H | H | 3-I | 2-$CH_3$-4-$CF_2CF_3$ | 177 |
| 88 | $CH(C_2H_5)$—$CH_2OCH_3$ | H | H | 6-I | 2-$CH_3$-4-$CF_2CF_3$ | 198.3-201.0 |
| 89 | $CH_2CF_3$ | H | H | 6-I | 2-$CH_3$-4-$CF_2CF_3$ | 184.7-202.5 |
| 90 | i-$C_3H_7$ | H | H | 3-I | 3-N=C($CF_2CF_3$)O-4 | 214-216 |
| 91 | t-$C_4H_9$ | H | H | 3-I | 3-N=C($CF_2CF_3$)O-4 | 253-254 |
| 92 | i-$C_3H_7$ | H | H | 3-Cl | 2-F-4-$OCF_3$ | 126-128 |
| 93 | i-$C_3H_7$ | H | H | 3-I | 2-F-4-$OCF_3$ | 220-222 |
| 94 | i-$C_3H_7$ | H | H | 3-I | 2-$C_2H_5$-4-$OCF_3$ | 241-243 |
| 95 | t-$C_4H_9$ | H | H | 3-I | 2-$C_2H_5$-4-$OCF_3$ | 224-225 |
| 96 | i-$C_3H_7$ | H | H | 3-Cl-4-F | 2-$CH_3$-4-$OCF_3$ | 184-186 |
| 97 | i-$C_3H_7$ | H | H | 3-Cl-4-F | 2-$CH_3$-4-$CF(CF_3)_2$ | 200-201 |
| 98 | i-$C_3H_7$ | H | H | 5-I | 2-$CH_3$-4-$OCF_2CHF_2$ | 203-204 |
| 99 | i-$C_3H_7$ | H | H | 4-I | 2-$CH_3$-4-$CF(CF_3)_2$ | 215-216 |
| 100 | i-$C_3H_7$ | H | H | 3-I | 2-$CH_3$-4-C≡C—$C_4H_9$-t | 205 |
| 101 | i-$C_3H_7$ | H | H | 3-Cl | 2-$CH_3$-4-CN | 230 |
| 102 | i-$C_3H_7$ | H | H | 3-I | 2-F-4-$C_2F_5$ | 190 |
| 103 | i-$C_3H_7$ | H | H | 3-I | 2-Cl-4-$C_2F_5$ | 200 |
| 104 | i-$C_3H_7$ | H | H | 3-I | 2-$CF_3$-4-$C_2F_5$ | 255 |
| 105 | i-$C_3H_7$ | H | H | 3-I | 2-$OCH_3$-4-$C_2F_5$ | 152 |
| 106 | 2-TetFur | H | H | 3-Cl | 2-$CH_3$-4-$C_2F_5$ | 153 |
| 107 | 2-TetFur | H | H | 6-Cl | 2-$CH_3$-4-$C_2F_5$ | 130 |
| 108 | $CH_2$-4-Pyi | H | H | 3-Cl | 2-$CH_3$-4-$C_2F_5$ | 88 |
| 109 | $CH_2$-4-Pyi | H | H | 6-Cl | 2-$CH_3$-4-$C_2F_5$ | Paste |
| 110 | i-$C_3H_7$ | H | H | 3-I | 2-$C_2F_5$-4-$C_2F_5$ | 245 |
| 111 | i-$C_3H_7$ | H | H | H | 4-O-(2-Pym) | 246 |
| 112 | $C(CH_3)_2CH_2CH_3$ | H | H | 3-I | 2-$CH_3$-4-$C_2F_5$ | 193 |
| 113 | $C(CH_3)_2CH_2CH_3$ | H | H | 3-I | 2-$CH_3$-4-$OCF_3$ | 180 |
| 114 | $C(CH_3)_2CH_2CH_3$ | H | H | 3-I | 2-$CH_3$-4-$OCHF_2$ | 176-177 |
| 115 | i-$C_3H_7$ | H | H | 3-I | 2-Cl-4-$OCF_2$O-5 | 226 |
| 116 | i-$C_3H_7$ | H | H | 3-I | 2-Cl-3-$OCF_2CF_2$O-4 | 219 |
| 117 | $C(CH_3)_2CH_2Cl$ | H | H | 3-I | 2-$CH_3$-4-$C_2F_5$ | 168-169 |
| 118 | i-$C_3H_7$ | H | H | 3-I | 4-(2-$CH_3$-4-Thz) | 217 |
| 119 | i-$C_3H_7$ | H | H | 3-I | 4-(2-$CH_3$-4-Oxa) | 212 |
| 120 | i-$C_3H_7$ | H | H | 3-I | 4-(2-i-$C_3H_7$-4-Thz) | 199 |
| 121 | $CH(CH_3)$-2-Pyi | H | H | 3-I | 2-$CH_3$-4-$OCF_3$ | 158-161 |
| 122 | N(Ph)$COCF_3$ | H | H | 3-I | 2-$CH_3$-4-$C_2F_5$ | 239-241 |
| 123 | $CH(CH_3)$-2-Fur | H | H | 3-I | 2-$CH_3$-4-$C_3F_7$-i | 191 |
| 124 | $CH(CH_3)$-2-Thi | H | H | 3-I | 2-$CH_3$-4-$C_3F_7$-i | 159 |
| 125 | i-$C_3H_7$ | H | H | 3-$CF_3SO$ | 2-$CH_3$-4-$C_3F_7$-i | 211-213 |
| 126 | t-$C_4H_9$ | H | H | 3-I | 2-N=C($CF_3$)O-3 | 120 |
| 127 | i-$C_3H_7$ | H | H | 3-I | 2-$CH_3$-4-C($CH_3$)=$NOCH_3$ | 218 |
| 128 | t-$C_4H_9$ | H | H | 6-$CF_3S$ | 2-$CH_3$-4-$C_3F_7$-i | 245-247 |
| 129 | $C(CH_3)_2CH_2SCH_3$ | H | H | 3-I | 2-$CH_3$-4-$C_3F_7$-i | 205-206 |
| 130 | $C(CH_3)_2CH_2SO_2CH_3$ | H | H | 3-I | 2-$CH_3$-4-$C_3F_7$-i | 90-95 |
| 131 | $C(CH_3)_2CH_2SOCH_3$ | H | H | 3-I | 2-$CH_3$-4-$C_3F_7$-i | 88-90 |
| 132 | $CH(CH_3)CH_2SCH_3$ | H | H | 3-I | 2-$CH_3$-4-$C_3F_7$-i | 197-199 |
| 133 | $CH(CH_3)CH_2SO_2CH_3$ | H | H | 3-I | 2-$CH_3$-4-$C_3F_7$-i | 82 |
| 134 | $CH(CH_3)CH_2SOCH_3$ | H | H | 3-I | 2-$CH_3$-4-$C_3F_7$-i | 134 |
| 135 | $C(CH_3)_2CH_2SCH_3$ | H | H | 3-I | 2-Cl-4-$OCF_3$ | 166 |
| 136 | $C(CH_3)_2CH_2SO_2CH_3$ | H | H | 3-I | 2-Cl-4-$OCF_3$ | 141 |
| 137 | $C(CH_3)_2CH_2SO_2CH_3$ | H | H | 3-Br | 2-Cl-4-$OCF_3$ | 133 |
| 138 | $C(CH_3)_2CH_2SC_2H_5$ | H | H | 3-I | 2-$CH_3$-4-$C_2F_5$ | 188-189 |
| 139 | $C(CH_3)_2CH_2SO_2C_2H_5$ | H | H | 3-I | 2-$CH_3$-4-$C_2F_5$ | 120-122 |
| 140 | $C(CH_3)_2CH_2SOC_2H_5$ | H | H | 3-I | 2-$CH_3$-4-$C_2F_5$ | 125-126 |
| 141 | $C(CH_3)_2CH_2SCH_3$ | H | H | 3-Cl | 2-$CH_3$-4-$C_3F_7$-i | 199-200 |
| 142 | $CH(CH_3)CH_2SCH_3$ | H | H | 3-I | 2-Cl-4-$C_3F_7$-i | 190 |

In Table 1, "Ph" means a phenyl group, "c" means an alicyclic hydrocarbon group, "Pyi" means a pyridyl group, "Pym" means a pyrimidinyl group, "Fur" means a furyl group, "TetFur" means a tetrahydrofuryl group, "Thi" means a thienyl group, "Thz" means a thiazolyl group, and "Oxa" means an oxazolyl group.

As the compounds having an insecticidal, acaricidal or nematocidal activity, which the composition for noxious organisms-controlling agent of the present invention comprises, insecticidal compounds such as chloronicotinyl compounds, carbamate compounds, pyrethroid compounds, macrolide compounds, phosphorus compounds and the like can be referred to. Examples thereof include the following compounds indicated by their general names, however, the present invention is by no means limited by these compounds:

acetamiprid, pymetrozine, fenitrothion, acephate, carbaryl, methomyl, cartap, cyhalothrin, ethofenprox, teflubenzuron, flufenoxuron, tebufenozide, fenpyroximate, pyridaben, imidacloprid, buprofezin, BPMC (fenobucarb), malathion, methidathion, fenthion, diazinon, oxydeprofos, vamidothion, ethiophencarb, pirimicarb, permethrin, cypermethrin, bifenthrin, halfenprox, silafluofen, nitenpyram, chlorfluazuron, methoxyfenozide, tebufenpyrad, pyrimidifen, dicofol, propargite, hexythiazox, clofentezine, spinosad, milbemectin, BT (*bacillus thuringiensis*), indoxacarb, chlorfenapyr, fipronil, etoxazole, acequinocyl, pirimiphos-methyl, acrinathrin, quinomethionate, chlorpyrifos, avermectin, emamectin-benzoate, fenbutatin oxide, terbufos, ethoprophos, cadusafos, fenamiphos, fensulfothion, DSP, dichlofenthion, fosthiazate, oxamyl, isamidofos, fosthietan, isazofos, thionazin, benfuracarb, spirodiclofen, ethiofencarb, azinphos-methyl, disulfoton, methiocarb, oxydemetonmethyl, parathion, cyfluthrin, beta-cyfluthrin, tebupyrimfos, spiromesifen, endosulfan, amitraz, tralomethrin, acetoprole, ethiprole and the like.

Further, it is also possible to use the compounds mentioned above in combination with insecticides, acaricides and nematocides having the following general names or chemical names, or those disclosed in the following Patent Kokai gazettes, etc.:

ethion, trichlorfon (DEP), metamidophos, dichlorvos (DDVP), mevinphos, monocrotophos, dimethoate, formothion, mecarbam, thiometon, disulfoton, naled (BRP), methylparathion, cyanophos, diamodafos, albendazole, oxibendazole, fenbendazole, oxfendazole, propaphos, sulprofos, prothiofos, profenofos, isophenphos, temephos, phenthoate, dimethylvinphos, chlorfenvinphos, tetrachlorvinphos, phoxim, isoxathion, pyraclofos, chlorpyrifos-methyl, pyridafenthion, phosalone, phosmet, dioxabenzofos, quinalphos, pyrethrins, allethrin, prallethrin, resmethrin, permethrin, tefluthrin, fenpropathrin, alpha-cypermethrin, lambda-cyhalothrin, deltamethrin, fenvalerate, esfenvalerate, flucythrinate, fluvalinate, cycloprothrin, thiodicarb, aldicarb, alanycarb, metolcarb, xylylcarb, propoxur, fenoxycarb, fenothiocarb, bifenazate, carbofuran, carbosulfan, furathiocarb, diafenthiuron, diflubenzuron, hexaflumuron, novaluron, lufenuron, chlorfluazuron, cyhexatin, Oleic acid sodium salt, Potassium oleate, methoprene, hydroprene, binapacryl, amitraz, chlorobenzilate, brompropylate, tetradifon, bensultap, benzoximate, chromafenozide, endosulfan, diofenolan, tolfenpyrad, triazamate, nicotine-sulfate, thiacloprid, thiamethoxam, clothianidin, dinotefuran (MT I-446), fluazinam, pyriproxyfen, hydramethylnon, cyromazine, TPIC (tripropylisocyanurate), thiocyclam, fenazaquin, polynactins, azadirachtin, rotenone, Hydroxy propyl starch, mesulfenfos, phosphocarb, isoamidofos, aldoxycarb, metam-sodium, morantel tartrate, dazomet, levamisol, trichlamide, pyridalyl, 2-[2-(4-cyanophenyl)-1-(3-trifluoromethylphenyl)-ethylidene]-N-(4-trifluoromethoxyphenyl)hydrazine carboxamide and its E isomer, its Z isomer, and mixtures of E and Z isomers at arbitrary mixing ratios, and the substituted aminoquinazolinone (thion) derivatives or salts thereof disclosed in JP-A-8-325239 and Japanese Patent Application 2000-334700, etc.

When the phthalamide derivative specified by the present invention is combined with the second active ingredient of the present invention, namely one or more compounds selected from the compounds having an insecticidal, acaricidal or nematocidal activity and the composition thus obtained is used as a composition for noxious organisms-controlling agent, the amount of the active ingredient compounds in 100 parts by weight of the composition may be appropriately selected from a range of 0.1-50 parts by weight and preferably 1-20 parts by weight. In the active ingredient compounds, the ratio between the specified phthalamide and the one or more compounds selected from the compounds having an insecticidal, acaricidal or nematocidal activity may be appropriately selected from a range of 0.05-2,000 parts by weight and preferably 10-100 parts by weight of the one or more compounds having an insecticidal, acaricidal or nematocidal activity, per one part by weight of the specified phthalamide derivative.

When the composition for noxious organisms-controlling agent of the present invention is put to use, the composition is used in an appropriate solid, liquid or powdery form prepared according to the conventional method in the pesticide making. According to the need, adjuvants and the like are added to the composition at an appropriate ratio. The mixture is subjected to melting, suspending, mixing, impregnation, adsorption or adhesion, and then formed into an appropriate preparation form such as emulsion, powder, granule, wettable powder, flowable composition, etc. according to the purpose, and put to use.

The composition for noxious organisms-controlling agent of the present invention is suitable for controlling various agricultural, forestry and horticultural pests making harm to paddyfield rice plants, vegetables, fruit plants, flowers and ornamental plants and the like; pests making injury on stored grain; sanitary insect pests; nematodes, etc. As examples of the pests, the following can be referred to:

pests belonging to HETEROPTERA of HEMIPTERA such as plataspid bug (*Megacopta punctatissimum*), whitespotted larger spined bug (*Eysarcoris lewisi*), whitespotted bug (*Eysarcoris parvus*), southern green stink bug. (*Nezara viridula*), brownwinged green bug (*Plautia stali*), narrow squash bug (*Cletus puctiger*), rice bug (*Leptocorisa chinensis*), bean bug (*Riptortus clavatus*), rice leaf bug (*Togo hemipterus*), pear lace bug (*Stephanitis nashi*), azelea lace bug (*Stephanitis pyrioides*), pale green plant bug (*Apolygus spinolai*), sorghum plant bug (*Stenotus rubrovittalus*), rice leaf bug (*Trigonotylus coelestialium*), etc.;

pests belonging to HOMOPTERA such as grape leafhopper (*Arboridia apicalis*), tea green leafhopper (*Empoasca onukii*), green rice leafhopper (*Nephotettix cincticeps*), green rice leafhopper (*Nephotettix virescens*), small brown planthopper (*Laodelphax striatellus*), brown rice planthopper (*Nilaparvata lugens*), whitebacked rice planthopper (*Sogatella furcifera*), citrus psylla (*Diaphorina citri*), citrus spiny whitefly (*Aleurocanthus spiniferus*), silver leaf whitefly (*Bemisia argentifolli*), sweetpotato whitefly (*Bemisia tabaci*), citrus whitefly (*Dialeurodes citri*), greenhouse whitefly (*Trialeurodes vaporariorum*), grapeleaf louse (*Viteus vitifolli*), woolly apple aphid (*Eriosoma lanigerum*), spiraea aphid (*Aphis citricola*), cowpea aphid (*Aphis craccivora*), cotton aphid (*Aphis gossipii*), greenhouse-potato aphid (*Aulacorthum solani*), cabbage aphid (*Brevicoryne brassicae*), potato aphid (*Macrosiphum euphorbiae*), green peach aphid (*Myzus persicae*), oat bird-cherry aphid (*Rhopalosiphum padi*), japanese grain aphid (*Sitobion akebiae*), comstock mealybug (*Pseudococcus comstocki*), Inidan wax scale (*Ceroplastes ceriferus*), red scale (*Aonidiella aurantii*), San Jose scale (*Comstockaphis perniciosa*), mulberry scale (*Pseudaulacapsis pentagoa*), arrowedhead scale (*Unaspis yanonensis*), etc.;

pests belonging to LEOPIDOPTERA such as summer fruit fortrix (*Adoxophyes orana fasciata*), smaller tea tortrix (*Adoxophyes honmai*), apple tortrix (*Archips fuscocupreanus*), peach fruit moth (*Carposina niponensis*), oriental fruit moth (*Grapholita molesta*), oriental tea tortrix (*Homona magnanima*), tea leafroller (*Caloptilia theivora*), mugwort looper (*Ascotis selenaria*), grape berry moth (*Endopiza viteana*), codling moth (*Laspeyresia pomonella*), apple leafminer (*Phyllonorycter ringoniella*), apple leaf miner (*Lyonetia prunifoliella malinella*), citrus leafminer (*Phyllocnistis citrella*), diamondback moth (*Plutella xylostella*), pink bollworm (*Pectinophora gossypiella*), peach fruit moth (*Carposina niponensis*), rice stem borer (*Chilo supperssalis*), yellow rice borer (*Scirpophaga incertulas*), rice leafroller (*Cnaphalocrosis medinalis*), cabbage webworm (*Hellulla undalis*), Chinese yellow swallowtail (*Papilio xuthus*), common white (*Pieris rapae crucivora*), tent catapillar (*Malacosoma neustria testacea*), fall webworm (*Hyphantria cunea*), bluegrass webworm (*Parapediasia tererrella*), corn earworm (*Helicoverpa armigera*), Heliothis (*Heliothis* spp.), cutworm (*Agrotis segetum*), beet semi-looper (*Autographa nigrisigna*), cabbage armyworm (*Mamestra brassicae*), beat armyworm (*Spodoptera exigua*), common cutworm (*Spodoptera litura*), etc.;

pests belonging to COLEOPTERA such as cupreous chafer (*Anomala cuprea*), Japanese beetle (*Popillia japonica*), powderpost beetle (*Lyctus brunneus*), confused flour beetle (*Tribolium confusum*), twenty-eight-spotted ladybird (*Epilachna vigintioctopunctata*), whitespotted longicorn beetle (*Anoplophora malasiaca*), Japanese pine sawyer (*Monochamus alteratus*), azuki bean weevil (*Callosobruchus chinensis*), cucurbit leaf beetle (*Aulacophora femoralis*), rootworm (*Diabrotica* spp.), boll weevil (*Anthonomus grandis grandis*), Mexican beetle (*Epilachna varivestis*), Colorado leaf beetle (*Leptinotarsa decemlineata*), rice water weevil (*Lissorhoptrus oryzophylus*), rice leaf beetle (*Oulema oryzae*), hunting billbug (*Sphenophrus venatus vestitus*), etc.;

pests belonging to HYMENOPTERA such as cabbage sawfly (*Athalia rosae ruficornis*), rose argid sawfly (*Arge pagana*), Formica japonica, etc.;

pests belonging to DIPTERA such as rice leafminer (*Agromyza oryzae*), rice leafminer (*Hydrellia griseola*), legume leafminer (*Liriomyza trifolii*), onion maggot (*Delia antiqua*), house fly (*Musca domestica*), *Culex pipiens molestus*, house mosquito (*Culex pipiens pallens*), etc.;

pests belonging to THYSANOPTERA such as yellow tea thrips (*Scirtothrips dorsalis*), southern yellow thrips (*Thrips palmi*), onion thrips (*Thrips tabaci*), cirtus yellow thrips (*Frankliniella occidentalis*), etc.;

pests belonging to ISOPTERA such as Formosan subterranean termites (*Coptotermes formosanus*), japanese subterranean termite (*Reticulitermes speratus*), booklice (*Psocoptera*), *Liposcelis bostrychophilus*, etc.;

pests belonging to ORTHOPTERA such as rice grasshopper (*Oxya yezoensis*), mole crichet (*Gryllotalpa* sp.), American cockroach (*Periplaneta americana*), German cockroach (*Blattella germanica*), etc.;

pests belonging to ACARINA such as citrus red mite (*Panonychus citri*), fruit tree red spider mite (*Panonychus ulmi*), two-spotted spider mite (*Tetranychus urticae*), Kanzawa spider mite (*Tetranychus kanzawai*), southern false spider mite (*Brevipalpus phoenicis*), clover mite (*Bryobia praetiosa*), pink citrus rust mite (*Aculops pelekassi*), japanese pear rust mite (*Eriophyes chibaensis*), broad mite (*Polyphagotarsonemus latus*), bulb mite (*Rhizoglyphus robini*), mold mite (*Tyrophagus putrescentiae*), etc.;

pests belonging to TYLENCHIDA such as coffee root-lesion nematode (*Pratylenchus coffeae*), Cobb root-lesion nematode (*Pratylenchus penetrans*), potato cyst nematode (*Globodera rostochiensis*), southern root-knot nematode (*Meloidogyne incognita*), etc.;

pests belonging to DOLYLAMIDA such as needle nematode (*Longidorus* sp.), etc.; and pests belonging to GASTRPODA such as slug (*Incilaria bilineata*), etc.

The useful plants to which the composition for noxious organisms-controlling agent of the present invention can be applied are not particularly limited, and the following plants can be referred to as examples thereof:

cereals such as rice, barley, wheat, rye, oat, corn, etc.; beans and peas such as soybean, red bean, broad bean, pea, kidney-bean, peanut, etc.; fruit trees such as apple, citrus trees and fruits, pear, grape, peach, plum, cherry, walnut, chestnut, almond, banana, strawberry, etc.; leafy and fruit vegetables such as cabbage, tomato, spinach, broccoli, lettuce, onion, stone-leek, Spanish paprika, egg-plant, pepper, etc.; root crops such as carrot, potato, sweet potato, taro, radish, lotus rhizome, turnip, burdock, garlic, etc.; processing crops such as cotton, flax, beet, hop, sugar can, sugar beet, olive, gum, coffee, tobacco, tea, etc.; cucurbitaceous plants such as pumpkin, cucumber, musk melon, water melon, melon, etc.; pasture plants such as orchard grass, sorghum, timothy, clover, alfalfa, etc.; lawn grasses such as mascarenegrass, bent grass, etc.; perfumery crops such as lavender, rosemary, thyme, parsley, pepper, ginger, etc.; flowers and ornamental plants such as chrysanthemum, rose, carnation, orchid, etc.; garden-trees such as ginkgo tree, cherry tree, gold-leaf plant, etc.; and timber woods such as white fir, silver fir, pine, hatchet-leaved arbor-vitae, Japan cedar, Japanese eypress, etc.

In order to control various disease pests, the composition for noxious organisms-controlling agent of the present invention is applied to the plants on which appearance of the noxious organisms is expected, either as it is or in the form of a dilution or suspension in a proper quantity of water or the like at a dosage effective for the control of the noxious organisms. For instance, with the aim of controlling the appearance of noxious organisms on fruit trees, cereals and vegetables, the composition may be directly used for foliage treatment, or the composition may also be used for seed treatments such as immersion of seeds in the agent solution, seed coating, calper treatment or the like, or absorption from the root by soil treatment or the like, such as incorporation into total soil layer, row treatment, soil incorporation, cell seedling treatment, prickling-in-hole treatment, plant foot treatment, top dressing, nursery box application of rice, submerged application, etc. In addition, application of the composition to the nutrient solution in the water culture, the use by fumigation, and the injection into tree stalks, etc. are also usable.

Further, apart from the spraying treatment on stored grain pests, house pests, sanitary insect pests and forest pests, application to construction material of house, fumigation, bait, etc. are also adoptable.

As the method of treating seeds, a method of dipping seeds in a diluted or undiluted liquid preparation of the liquid or solid composition and thereby making the agent permeate into the seeds; a method of mixing a solid or liquid preparation with seeds for the sake of powder coating and thereby making the agent adhere to the seed surface; a method of mixing the preparation with an adhesive carrier such as resin, polymer or the like and coating seeds with such an adhesive mixture; a method of spraying the preparation to the neighborhood of seeds simultaneously with planting, etc. can be referred to.

The term "seed" to be treated with the composition of the present invention means a plant body of the initial stage of cultivation used for reproduction of plants, and involves not only the seeds but also plant bodies for nutrient reproduction such as bulb, tuber, seed tuber, aerial tuber, scaly bulb, stalks for cuttage, and the like.

The term "soil" or "cultivation carrier" for plants in the practice of the using method of the present invention means a support for use in culture of a plant and especially a support in which roots are to be grown. They are not limited in material quality, but any material may be used so far as a plant can be grown therein. For instance, so-called various soils, nursery mat, water and the like can be used. Specific examples of the material constituting the soil or cultivation carrier include sand, pumice, vermiculite, diatomaceous earth, agar, gelatinous materials, polymeric materials, rock wool, glass wool, wood chips, bark and the like.

As method for spraying the composition to foliage part of crops or stored grain pest, sanitary insect pest, forest pest, etc., a method of diluting a liquid preparation such as emulsifiable concentrate, flowable agent and the like or a solid preparation such as wettable preparation, granular wettable preparation and the like with water properly and spraying the dilution, a method of spraying a powdery composition, a method of fumigation, etc. can be referred to.

As method for applying the composition to the soil, a method of applying a liquid preparation either diluted or undiluted with water to the plant foot, nursery bed for raising seedlings or the like, a method of spraying a granular agent to the plant foot or nursery bed, a method of spraying a dust, a wettable powder, a wettable granule or a granular agent to the soil and mixing it with the whole soil either before seeding or before transplantation, a method of spraying a dust, a wettable powder, a wettable granule, a granular agent or the like to planting holes, planting rows, etc can be referred to.

As method for applying the composition to a nursery box of paddyfield rice, a method of applying the composition in the form of dust, granular wettable powder, granule, etc. can be referred to, though the preparation form may vary depending on the time of application, namely whether the application is carried out in sowing period, greening period or transplanting period. It is also possible to apply the composition in the form of a mixture with soil, as in the form of mixture of soil and a dust, a granular wettable powder or a granule, according to a method of mixing into bed soil, covering soil, or the whole soil. It is also possible to apply the composition by merely making the soil and various preparations into layers.

For applying the composition of the present invention to a paddy field, a solid preparation such as jumbo-pack, granule, wettable granule, and the like or a liquid preparation such as flowable, emulsifiable concentrate and the like is scattered to a paddy field usually in a submerged state. Otherwise, it is also possible to scatter or inject an appropriate agent as it is or in the form of a mixture with fertilizers into soil at the time of transplantation. It is further possible to apply an emulsifiable concentrate to the water inlet or water flow source of irrigating system, by which the composition can be applied together with water supplied to the paddy field in a labor-saving manner.

In case of upland field crops, the composition of the present invention may be applied to the cultivation carrier surrounding the seeds or plant bodies in the period from the seeding to the seedling raising. In cases where plant seeds are directly sown to the field, the composition may directly be applied to seeds to make a seed coating, or may also be applied to the base of hills in the course of cultivation to achieve a successful result. It is also possible to scatter a granular preparation or to apply a liquid preparation after dilution with water or without dilution. Another preferable treatment is to mix a granular preparation with a cultivation carrier before seeding and to sow seeds thereafter.

In cases where cultured plants to be transplanted are treated at the seeding time or in the seedling raising period, it is preferable to treat the seeds directly, or to carry out an irrigating treatment of a seedling raising bed with a liquefied agent, or to carry out a powdering treatment thereof with a granular agent. Further, it is also preferable to apply a granular agent to the planting holes at the time of set-planting or to mix the agent into the cultivation carrier in the neighborhood of the sites of transplantation.

The composition for noxious organisms-controlling agent of the present invention may be put to use after forming it into a usual preparation form, such as emulsifiable concentrate, wettable powder, granular wettable powder, flowable preparation, solution, granule, dust, fumigant and the like. Although the dosage thereof varies depending on the content of active ingredient in the composition, climate conditions, preparation form, method of application, place of application, objective noxious organism to be controlled, objective crop plant, etc. The dosage may be appropriately selected from a range of 0.1 gram to 1,000 grams and preferably 1 gram to 500 grams in terms of weight of active ingredient, per are of the field. In the case of seed treatment, it is possible to use the composition in an amount of 0.01-50% and preferably in an amount of 0.1-10% in terms of weight of active ingredient, based on the weight of seed. In cases where an emulsifiable concentrate or a wettable powder is diluted with water and then put to use, the concentration at the time of application is 0.00001-0.1%. In the cases of a granular preparation, a dust, and a liquid composition to be applied to seeds, the composition is directly applied without dilution, usually.

For the purpose of controlling the diseases and/or the weeds which appear simultaneously with the time of the application of the composition for noxious organisms-controlling agent of the present invention, the second active ingredient of the present invention, namely the compound having an insecticidal, acaricidal or nematocidal activity, may be replaced with a compound having a fungicidal or herbicidal activity. By taking such a measure, the span of objective disease and pests to be controlled can be expanded and the dosage can be reduced, and the herbicidal effect can be increased synergistically. The same effect as above can be expected also by adding a compound having a fungicidal or herbicidal activity to the composition for noxious organisms-controlling agent of the present invention and putting the mixture thus obtained to use.

As said compound having a fungicidal or herbicidal activity, the following can be referred to.

Thus, examples of the compound having a fungicidal activity include azoxystrobin, diclocymet, pyroquilon, kasugamycin, IBP (iprobenfos), hymexazol, mepronil, tricyclazole, edifenphos, isoprothiolane, blasticidin, flutolanil, diclomezine, pencycuron, carbendazim, dodine, propamocarb, pyrimethanil, fluquinconazole, fosetyl-AL, bromoconazole, triticonazole, flumetover, fenamidone, tolylfluanid, dichlofluanid, trifloxystrobin, triadimenol, spiroxamine, fenhexamid, iprovalicarb, fthalide, iprodione, thiophanate, benomyl, triflumizole, fluazinam, zineb, captan, manzeb, fenarimol, calcium polysulfide, triadimefon, vinclozolin, dithianon, bitertanol, polycarbamate, iminoctadine-DBS, pebulate, polyoxin-B, propineb, chinomethionat, dichlofluanid, chlorothalonil, difenoconazole, fluoroimide, triforine, oxadixyl, streptomycin, mancozeb, oxolinic acid, mepronil, metalaxyl, propiconazole, hexaconazole, sulfur, pyrifenox, basic copper sulfate, pyrimethanil, iprobenfos, tolclofos-methyl, maneb, thiophanatemethyl, thifluzamide, furametpyr, flusulfamide, kresoxim-methyl, carpropamid, hydroxyisoxazole, echlomezole, procymidone, vinclozolin, ipconazole, furconazole, myclobutanil, tetraconazole, tebuconazole, imibenconazole, prochloraz, pefurazoate, cyproconazole, mepanipyrim, thiadiazin, probenazole, acibenzolar-S-methyl, validamycin(-A), fenoxanil, N-(3-chloro-4-methylphenyl)-4-methyl-1,2,3-thiadiazole-5-carboxamide, etc.

Examples of the compound having a herbicidal activity include bensulfuron-methyl, azimsulfuron, cinosulfuron, cyclosulfamuron, pyrazosulfuron-ethyl, imazosulfuron, indanofan, cyhalofop-butyl, thenylchlor, esprocarb, etobenzanid, cafenstrole, clomeprop, dimethametryn, daimuron, bifenox, pyributicarb, pyriminobac-methyl, pretilachlor, bromobutide, benzofenap, benthiocarb, bentoxazone, benfuresate, mefenacet, fenoxaprop-P-ethyl, phenmedipham, diclofopmethyl, desmedipham, ethofumesate, isoproturon, amidosulfuron, anilofos, ethoxysulfuron, iodosulfuron, isoxadifen, foramsulfuron, pyraclonil, mesosulfuron, diuron, neburon, dinoterb, carbetamide, bromoxynil, oxadiazon, dimefuron, diflufenican, aclonifen, benzofenap, oxaziclomefone, isoxaflutole, oxadiargyl, flurtamone, metribuzin, methabenzthiazuron, tribufos, metamitron, ethiozin, flufenacet, sulcotrion, fentrazamide, propoxycarbazone, flucarbazone, metosulam, amicarbazone, etc.

Further, it is also possible to mix the herbicides expressed by the following general names into the composition of this invention:

glyphosate-isopropyl amine, glyphosate-trimesium, glufosinate-ammonium, bialaphos, butamifos, prosulfocarb, asulam, linuron, calcium peroxide, alachlor, pendimethalin, acifluofen-sodium, lactofen, ioxynil-octanoate, alloxydim, sethoxydim, napropamide, pyrazolate, pyraflufen-ethyl, imazapyr, sulfentrazone, oxadiazon, paraquat, diquat, simazine, atrazine, fluthiacet-methyl, quizalofop-ethyl, bentazone (BAS-3510-H), triaziflam, etc.

Further, the composition of the present invention can be used in the form of a mixture with the following compounds having a plant growth regulating activity:

thidiazuron, mefenpyr, ethephon, cyclanilide, etc.

The composition of this invention can be used as a mixture with the following biotic pesticides to exhibit a similar effect:

viral preparations such as Nuclear polyhedrosis virus (NPV), Granulosis virus (GV), Cytoplastic polyhedrosis virus (CPV), Entomopox virus (EPV), etc.:

microbial pesticides used as insecticide or nematocide such as *Monacrosporium phymatophagum, Steinernema caprocapsae, Steinernema kushidai, Pasteuria penetrans*, etc.;

microbial pesticides used as fungicide such as *Trichoderma lignorum, Agrobacterium radiobactor, Erwinia carotovora, Bacillus subtilis*, monacrosporium-phamatophagum etc.; and microial pesticides used as herbicide such as *Xanthomonas capestris*, etc.

Further, it is also possible to use the composition of the present invention in combination with the following biotic pesticides:

natural enemy organisms such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.;

microbial pesticides such as *Beauveria brongniartii*), etc.; and pheromones such as (Z)-10-tetradecenyl=acetate, (E,Z)-4,10-tetradecadienyl=acetate, (Z)-8-dodecenyl=acetate, (Z)-11-tetradecenyl=acetate, (Z)-13-icosen-10-one, (Z)-8-dodecenyl=acetate, (Z)-11-tetradecenyl=acetate, (Z)-13-icosen-10-one, 14-methyl-1-octadecene, etc.

EXAMPLES

Next, typical examples and test examples of the present invention are mentioned below. This invention is by no means limited by these examples. In the examples, the terms "part" and "parts" are both by weight.

Example 1

| | |
|---|---|
| Compound of Table 1 | 5 parts |
| Fenpyroximate | 10 parts |
| Silicic acid hydrate | 30 parts |
| Hitenol N-08 (manufactured by Daiichi Kogyo Seiyaku) | 5 parts |
| Calcium ligninsulfonate | 3 parts |
| Wettable clay | 47 parts |

After impregnating silicic acid hydrate with the active ingredient compounds, the silicic acid hydrate is uniformly blended with other ingredients to form a wettable powder composition.

Example 2

| | |
|---|---|
| Compound of Table 1 | 10 parts |
| Tebufenpyrad | 10 parts |
| Sorpol 3105 (manufactured by Toho Yakuhin Kogyo) | 5 parts |
| Propylene glycol | 5 parts |
| Rhodopol (manufactured by Rohne Poulenc Inc.) | 2 parts |
| Water | 68 parts |

The above-mentioned ingredients are uniformly mixed together and dispersed in water to form a flowable preparation.

Example 3

| Compound of Table 1 | 10 parts |
|---|---|
| Isoprothiolane | 20 parts |
| SP-3005X (manufactured by Toho Kagaku) | 15 parts |
| Xylene | 35 parts |
| N-Methylpyrrolidone | 20 parts |

The above-mentioned ingredients are uniformly mixed and melted to form an emulsifiable concentrate.

Example 4

| Compound of Table 1 | 10 parts |
|---|---|
| Tebufenozide | 20 parts |
| Sorpol 3105 | 5 parts |
| Propylene glycol | 2 parts |
| Rhodopol 23 | 1 part |
| Water | 62 parts |

The above-mentioned ingredients are uniformly mixed together and dispersed in water to form a flowable preparation.

Example 5

| Compound of Table 1 | 10 parts |
|---|---|
| Buprofezin | 5 parts |
| Silicic acid hydrate | 34 parts |
| Hitenol N-08 | 3 parts |
| Demol T | 2 parts |
| Calcium carbonate powder | 46 parts |

After impregnating silicic acid hydrate with the active ingredient compounds, the silicic acid hydrate is uniformly blended with other ingredients to form a wettable powder composition.

Example 6

| Compound of Table 1 | 10 parts |
|---|---|
| Pyridaben | 15 parts |
| SP-3005X | 15 parts |
| Xylene | 40 parts |
| N-Methylpyrrolidone | 20 parts |

The above-mentioned ingredients are uniformly mixed together and melted to form an emulsifiable concentrate.

Example 7

| Compound of Table 1 | 10 parts |
|---|---|
| Pyraflufen-ethyl | 20 parts |
| Sorpol 3105 | 5 parts |
| Propylene glycol | 2 parts |
| Rhodopol 23 | 0.5 part |
| Water | 62.5 parts |

The above-mentioned ingredients are uniformly mixed together and dispersed in water to form a flowable preparation.

Example 8

| Compound of Table 1 | 10 parts |
|---|---|
| Acetamiprid | 5 parts |
| Sorpol 3105 | 5 parts |
| Propylene glycol | 3 parts |
| Rhodopol | 2 parts |
| Water | 75 parts |

The above-mentioned ingredients are uniformly mixed together and dispersed in water to form a flowable preparation.

Example 9

| Compound of Table 1 | 10 parts |
|---|---|
| Imidacloprid | 10 parts |
| SP-3005X | 15 parts |
| Xylene | 45 parts |
| N-Methylpyrrolidone | 20 parts |

The above-mentioned ingredients are uniformly mixed together and melted to form an emulsifiable concentrate.

Example 10

| Compound of Table 1 | 5 parts |
|---|---|
| Chlorfenapyr | 10 parts |
| Sorpol 3105 | 5 parts |
| Propylene glycol | 3 parts |
| Rhodopol 23 | 2 parts |
| Water | 75 parts |

The above-mentioned ingredients are uniformly mixed together and dispersed in water to form a flowable preparation.

Example 11

| Compound of Table 1 | 5 parts |
|---|---|
| Pymetrozine | 10 parts |
| Sorpol 3105 | 5 parts |
| Propylene glycol | 3 parts |
| Rhodopol 23 | 2 parts |
| Water | 75 parts |

The above-mentioned ingredients are uniformly mixed together and dispersed in water to form a flowable preparation.

Test Example 1

Insecticidal Test on Smaller Tea Tortrix (*Adoxophyes Orana Fosciota*)

Tea leaves were dipped in a solution of a chemical diluted to a prescribed concentration for 30 seconds. After air-dryness, the leaves were transferred to a plastic dish having a diameter of 9 cm, inoculated with ten 4th instar larvae of smaller tea tortrix, and left to stand in a thermostatted chamber at 25° C. Four days and seven days after the treatment, the number of alive insects were counted, from which percentage of death was calculated. The test was carried out with two replications of 10 insects. The results are shown in Table 2.

TABLE 2

| Test agent | | Concentration (ppm) | Death rate (%) After 4 days | Death rate (%) After 7 days |
|---|---|---|---|---|
| Compound 19 | + chlorpyriphos | 0.3 + 1 | 35 | 75 |
| | + chlorfluazuron | 0.3 + 1 | 35 | 95 |
| | + chlorfenapyr | 0.3 + 1 | 30 | 75 |
| | + emamectin-benzoate | 0.3 + 0.1 | 25 | 85 |
| | + methoxyfenozide | 0.3 + 0.1 | 75 | 95 |
| | + indoxacarb | 0.3 + 1 | 55 | 95 |
| | + fenpyroximate | 0.3 + 50 | 30 | 85 |
| Compound 20 | + chlorpyriphos | 0.3 + 1 | 20 | 45 |
| | + chlorfluazuron | 0.3 + 1 | 25 | 85 |
| | + chlorfenapyr | 0.3 + 1 | 20 | 75 |
| | + emamectin-benzoate | 0.3 + 0.1 | 25 | 75 |
| | + methoxyfenozide | 0.3 + 0.1 | 45 | 85 |
| | + indoxacarb | 0.3 + 1 | 45 | 75 |
| | + fenpyroximate | 0.3 + 50 | 30 | 80 |
| Compound 39 | + chlorpyriphos | 0.3 + 1 | 15 | 45 |
| | + chlorfluazuron | 0.3 + 1 | 20 | 75 |
| | + chlorfenapyr | 0.3 + 1 | 15 | 70 |
| | + emamectin-benzoate | 0.3 + 0.1 | 20 | 70 |
| | + methoxyfenozide | 0.3 + 0.1 | 40 | 80 |
| | + indoxacarb | 0.3 + 1 | 40 | 70 |
| | + fenpyroximate | 0.3 + 50 | 25 | 75 |
| Compound 40 | + chlorpyriphos | 0.3 + 1 | 20 | 45 |
| | + chlorfluazuron | 0.3 + 1 | 25 | 80 |
| | + chlorfenapyr | 0.3 + 1 | 15 | 70 |
| | + emamectin-benzoate | 0.3 + 0.1 | 20 | 70 |
| | + methoxyfenozide | 0.3 + 0.1 | 35 | 85 |
| | + indoxacarb | 0.3 + 1 | 35 | 75 |
| | + fenpyroximate | 0.3 + 50 | 20 | 70 |
| Compound 41 | + chlorpyriphos | 0.3 + 1 | 40 | 80 |
| | + chlorfluazuron | 0.3 + 1 | 35 | 95 |
| | + chlorfenapyr | 0.3 + 1 | 30 | 75 |
| | + emamectin-benzoate | 0.3 + 0.1 | 30 | 100 |
| | + methoxyfenozide | 0.3 + 0.1 | 75 | 95 |
| | + indoxacarb | 0.3 + 1 | 55 | 95 |
| | + fenpyroximate | 0.3 + 50 | 35 | 90 |
| Compound 42 | + chlorpyriphos | 0.3 + 1 | 45 | 85 |
| | + chlorfluazuron | 0.3 + 1 | 35 | 100 |
| | + chlorfenapyr | 0.3 + 1 | 30 | 85 |
| | + emamectin-benzoate | 0.3 + 0.1 | 30 | 100 |
| | + methoxyfenozide | 0.3 + 0.1 | 75 | 95 |
| | + indoxacarb | 0.3 + 1 | 55 | 95 |
| | + fenpyroximate | 0.3 + 50 | 30 | 85 |
| Compound 43 | + chlorpyriphos | 0.3 + 1 | 45 | 85 |
| | + chlorfluazuron | 0.3 + 1 | 35 | 95 |
| | + chlorfenapyr | 0.3 + 1 | 30 | 85 |
| | + emamectin-benzoate | 0.3 + 0.1 | 30 | 100 |
| | + methoxyfenozide | 0.3 + 0.1 | 75 | 95 |
| | + indoxacarb | 0.3 + 1 | 50 | 95 |
| | + fenpyroximate | 0.3 + 50 | 35 | 90 |
| Compound 44 | + chlorpyriphos | 0.3 + 1 | 25 | 65 |
| | + chlorfluazuron | 0.3 + 1 | 30 | 85 |
| | + chlorfenapyr | 0.3 + 1 | 25 | 80 |
| | + emamectin-benzoate | 0.3 + 0.1 | 25 | 75 |
| | + methoxyfenozide | 0.3 + 0.1 | 45 | 90 |
| | + indoxacarb | 0.3 + 1 | 45 | 80 |
| Compound 45 | + chlorpyriphos | 0.3 + 1 | 30 | 75 |
| | + chlorfluazuron | 0.3 + 1 | 25 | 90 |
| | + chlorfenapyr | 0.3 + 1 | 20 | 75 |
| | + emamectin-benzoate | 0.3 + 0.1 | 30 | 80 |
| | + methoxyfenozide | 0.3 + 0.1 | 35 | 85 |
| | + indoxacarb | 0.3 + 1 | 35 | 75 |
| Compound 46 | + chlorpyriphos | 0.3 + 1 | 20 | 65 |
| | + chlorfluazuron | 0.3 + 1 | 35 | 80 |
| | + chlorfenapyr | 0.3 + 1 | 20 | 75 |
| | + emamectin-benzoate | 0.3 + 0.1 | 25 | 85 |
| | + methoxyfenozide | 0.3 + 0.1 | 35 | 85 |
| | + indoxacarb | 0.3 + 1 | 40 | 75 |
| Compound 47 | + chlorpyriphos | 0.3 + 1 | 40 | 80 |
| | + chlorfluazuron | 0.3 + 1 | 40 | 95 |
| | + chlorfenapyr | 0.3 + 1 | 35 | 95 |
| | + emamectin-benzoate | 0.3 + 0.1 | 40 | 95 |
| | + methoxyfenozide | 0.3 + 0.1 | 75 | 100 |
| | + indoxacarb | 0.3 + 1 | 45 | 90 |
| | + fenpyroximate | 0.3 + 50 | 35 | 95 |
| Compound 48 | + chlorpyriphos | 0.3 + 1 | 25 | 75 |
| | + chlorfluazuron | 0.3 + 1 | 35 | 85 |
| | + chlorfenapyr | 0.3 + 1 | 35 | 80 |
| | + emamectin-benzoate | 0.3 + 0.1 | 30 | 90 |
| | + methoxyfenozide | 0.3 + 0.1 | 40 | 75 |
| | + indoxacarb | 0.3 + 1 | 35 | 80 |
| Compound 54 | + chlorpyriphos | 0.3 + 1 | 30 | 80 |
| | + chlorfluazuron | 0.3 + 1 | 25 | 85 |
| | + chlorfenapyr | 0.3 + 1 | 30 | 85 |
| | + emamectin-benzoate | 0.3 + 0.1 | 30 | 95 |
| | + methoxyfenozide | 0.3 + 0.1 | 35 | 80 |
| | + indoxacarb | 0.3 + 1 | 30 | 85 |
| Compound 129 | + chlorpyriphos | 0.1 + 1 | 35 | 75 |
| | + chlorfluazuron | 0.1 + 1 | 35 | 95 |
| | + chlorfenapyr | 0.1 + 1 | 30 | 75 |
| | + emamectin-benzoate | 0.1 + 0.1 | 25 | 85 |
| | + methoxyfenozide | 0.1 + 0.1 | 75 | 95 |
| | + indoxacarb | 0.1 + 1 | 55 | 95 |
| | + fenpyroximate | 0.1 + 50 | 30 | 85 |
| Compound 130 | + chlorpyriphos | 0.1 + 1 | 35 | 75 |
| | + chlorfluazuron | 0.1 + 1 | 35 | 95 |
| | + chlorfenapyr | 0.1 + 1 | 30 | 75 |
| | + emamectin-benzoate | 0.1 + 0.1 | 25 | 85 |
| | + methoxyfenozide | 0.1 + 0.1 | 75 | 95 |
| | + indoxacarb | 0.1 + 1 | 55 | 95 |
| | + fenpyroximate | 0.1 + 50 | 30 | 85 |
| Compound 131 | + chlorpyriphos | 0.1 + 1 | 35 | 75 |
| | + chlorfluazuron | 0.1 + 1 | 35 | 95 |
| | + chlorfenapyr | 0.1 + 1 | 30 | 75 |
| | + emamectin-benzoate | 0.1 + 0.1 | 25 | 85 |
| | + methoxyfenozide | 0.1 + 0.1 | 75 | 95 |
| | + indoxacarb | 0.1 + 1 | 55 | 95 |
| | + fenpyroximate | 0.1 + 50 | 30 | 85 |
| Compound 19 | | 0.3 | 0 | 30 |
| Compound 20 | | 0.3 | 0 | 25 |
| Compound 39 | | 0.3 | 0 | 20 |
| Compound 40 | | 0.3 | 0 | 25 |
| Compound 41 | | 0.3 | 0 | 30 |
| Compound 42 | | 0.3 | 0 | 30 |
| Compound 43 | | 0.3 | 0 | 35 |
| Compound 44 | | 0.3 | 0 | 20 |
| Compound 45 | | 0.3 | 0 | 25 |
| Compound 46 | | 0.3 | 0 | 15 |
| Compound 47 | | 0.3 | 0 | 30 |
| Compound 48 | | 0.3 | 0 | 25 |
| Compound 54 | | 0.3 | 0 | 25 |
| Compound 129 | | 0.1 | 10 | 30 |
| Compound 130 | | 0.1 | 10 | 25 |
| Compound 131 | | 0.1 | 5 | 20 |
| chlorpyriphos | | 1 | 10 | 10 |
| chlorfluazuron | | 1 | 10 | 30 |
| chlorfenapyr | | 1 | 0 | 0 |

TABLE 2-continued

| Test agent | Concentration (ppm) | Death rate (%) After 4 days | Death rate (%) After 7 days |
|---|---|---|---|
| emamectin-benzoate | 0.1 | 10 | 45 |
| methoxyfenozide | 0.1 | 0 | 50 |
| indoxacarb | 1 | 10 | 40 |
| fenpyroximate | 50 | 0 | 0 |
| Untreated plot | — | 0 | 0 |

Test Example 2

Insecticidal Test on Green Peach Aphid (*Myzus Persicae*)

Chinese cabbage plants (variety: Aichi) were planted in plastic pots having a diameter of 8 cm and a height of 8 cm, on which green peach aphids were inoculated. Then, a solution of an agent which had been diluted to a predetermined concentration was thoroughly sprayed to the leaves and stalks. After air-dryness, the pots were left to stand in a green house. Six days after the spraying treatment, the number of the insects parasitic on each Chinese cabbage plant was counted, from which the control value was calculated according to the following equation. The test was carried out with two replications on one pot per one plot.

Controlling value=100−{(Ta×Cb)/(Tb×Ca)}×100

Ta: Number of parasitic insects after spraying in the treated plot
Tb: Number of parasitic insects before spraying in the treated plot
Ca: Number of parasitic insects after spraying in the untreated plot
Cb: Number of parasitic insects before spraying in the untreated plot
The results are shown in Table 3.

TABLE 3

| Test agent | | Concentration (ppm) | Control degree (%) |
|---|---|---|---|
| Compound 19 | + Acephate | 100 + 10 | 81 |
| | + imidacloprid | 100 + 0.1 | 100 |
| | + bifenthrin | 100 + 0.1 | 100 |
| | + flufenoxuron | 100 + 50 | 43 |
| | + pyridaben | 100 + 10 | 92 |
| | + milbemectin | 100 + 1 | 100 |
| Compound 20 | + Acephate | 100 + 10 | 81 |
| | + imidacloprid | 100 + 0.1 | 100 |
| | + bifenthrin | 100 + 0.1 | 100 |
| | + flufenoxuron | 100 + 50 | 52 |
| | + pyridaben | 100 + 10 | 92 |
| | + milbemectin | 100 + 1 | 94 |
| Compound 39 | + Acephate | 100 + 10 | 83 |
| | + imidacloprid | 100 + 0.1 | 97 |
| | + bifenthrin | 100 + 0.1 | 100 |
| | + flufenoxuron | 100 + 50 | 48 |
| | + pyridaben | 100 + 10 | 92 |
| | + milbemectin | 100 + 1 | 94 |
| Compound 40 | + Acephate | 100 + 10 | 86 |
| | + imidacloprid | 100 + 0.1 | 100 |
| | + bifenthrin | 100 + 0.1 | 100 |
| | + flufenoxuron | 100 + 50 | 48 |
| | + pyridaben | 100 + 10 | 92 |
| | + milbemectin | 100 + 1 | 100 |
| Compound 41 | + Acephate | 100 + 10 | 95 |
| | + imidacloprid | 100 + 0.1 | 100 |
| | + bifenthrin | 100 + 0.1 | 100 |
| | + flufenoxuron | 100 + 50 | 60 |
| | + pyridaben | 100 + 10 | 88 |
| | + milbemectin | 100 + 1 | 98 |
| Compound 42 | + Acephate | 100 + 0 | 95 |
| | + imidacloprid | 100 + 0.1 | 100 |
| | + bifenthrin | 100 + 0.1 | 100 |
| | + flufenoxuron | 100 + 50 | 55 |
| | + pyridaben | 100 + 10 | 90 |
| | + milbemectin | 100 + 1 | 100 |
| Compound 43 | + Acephate | 100 + 10 | 90 |
| | + imidacloprid | 100 + 0.1 | 95 |
| | + bifenthrin | 100 + 0.1 | 100 |
| | + flufenoxuron | 100 + 50 | 60 |
| | + pyridaben | 100 + 10 | 85 |
| | + milbemectin | 100 + 1 | 100 |
| Compound 44 | + Acephate | 100 + 10 | 75 |
| | + imidacloprid | 100 + 0.1 | 80 |
| | + bifenthrin | 100 + 0.1 | 95 |
| | + flufenoxuron | 100 + 50 | 55 |
| | + pyridaben | 100 + 10 | 73 |
| | + milbemectin | 100 + 1 | 93 |
| Compound 45 | + Acephate | 100 + 10 | 70 |
| | + imidacloprid | 100 + 0.1 | 78 |
| | + bifenthrin | 100 + 0.1 | 93 |
| | + flufenoxuron | 100 + 50 | 61 |
| | + pyridaben | 100 + 10 | 78 |
| | + milbemectin | 100 + 1 | 98 |
| Compound 46 | + Acephate | 100 + 10 | 65 |
| | + imidacloprid | 100 + 0.1 | 75 |
| | + bifenthrin | 100 + 0.1 | 94 |
| | + flufenoxuron | 100 + 50 | 55 |
| | + pyridaben | 100 + 10 | 68 |
| | + milbemectin | 100 + 1 | 95 |
| Compound 47 | + Acephate | 100 + 10 | 78 |
| | + imidacloprid | 100 + 0.1 | 88 |
| | + bifenthrin | 100 + 0.1 | 94 |
| | + flufenoxuron | 100 + 50 | 58 |
| | + pyridaben | 100 + 10 | 75 |
| | + milbemectin | 100 + 1 | 94 |
| Compound 48 | + Acephate | 100 + 10 | 66 |
| | + imidacloprid | 100 + 0.1 | 93 |
| | + bifenthrin | 100 + 0.1 | 96 |
| | + flufenoxuron | 100 + 50 | 48 |
| | + pyridaben | 100 + 10 | 75 |
| | + milbemectin | 100 + 1 | 90 |
| Compound 54 | + Acephate | 100 + 10 | 65 |
| | + imidacloprid | 100 + 0.1 | 92 |
| | + bifenthrin | 100 + 0.1 | 89 |
| | + flufenoxuron | 100 + 50 | 55 |
| | + pyridaben | 100 + 10 | 73 |
| | + milbemectin | 100 + 1 | 95 |
| Compound 129 | + Acephate | 100 + 10 | 85 |
| | + imidacloprid | 100 + 0.1 | 100 |
| | + bifenthrin | 100 + 0.1 | 100 |
| | + flufenoxuron | 100 + 50 | 45 |
| | + pyridaben | 100 + 10 | 90 |
| | + milbemectin | 100 + 1 | 100 |
| Compound 130 | + Acephate | 100 + 10 | 87 |
| | + imidacloprid | 100 + 0.1 | 100 |
| | + bifenthrin | 100 + 0.1 | 100 |
| | + flufenoxuron | 100 + 50 | 54 |
| | + pyridaben | 100 + 10 | 96 |
| | + milbemectin | 100 + 1 | 95 |
| Compound 131 | + Acephate | 100 + 10 | 81 |
| | + imidacloprid | 100 + 0.1 | 99 |
| | + bifenthrin | 100 + 0.1 | 97 |
| Compound 19 | | 100 | 0 |
| Compound 20 | | 100 | 0 |
| Compound 39 | | 100 | 0 |
| Compound 40 | | 100 | 0 |
| Compound 41 | | 100 | 0 |
| Compound 42 | | 100 | 0 |

TABLE 3-continued

| Test agent | Concentration (ppm) | Control degree (%) |
|---|---|---|
| Compound 43 | 100 | 0 |
| Compound 44 | 100 | 0 |
| Compound 45 | 100 | 0 |
| Compound 46 | 100 | 0 |
| Compound 47 | 100 | 0 |
| Compound 48 | 100 | 0 |
| Compound 54 | 100 | 0 |
| Compound 129 | 100 | 5 |
| Compound 130 | 100 | 10 |
| Compound 131 | 100 | 0 |
| acephate | 10 | 48 |
| imidacloprid | 0.1 | 69 |
| bifenthrin | 0.1 | 80 |
| flufenoxuron | 50 | 11 |
| pyridaben | 10 | 43 |
| milbemectin | 1 | 82 |

Test Example 3

Insecticidal Test on Brown Rice Planthopper (*Nilaparvata Lugens*)

Rice seedlings (variety: Nihombare) were dipped in a solution of an agent diluted to a predetermined concentration for 30 seconds. After air-dryness, each seedling was introduced into a glass-made test tube having a diameter of 1.8 cm and a height of 20 cm, and inoculated with ten 3rd inster nimphs of brown rice planthopper. Then, the test tube was stoppered with cotton. One day after and four days after the treatment., the number of alive insects was counted, based on which the insect death rate was calculated. The test was carried out with two replications of 10 heads.

The results are shown in Table 4.

TABLE 4

| Test agent | | Concentration (ppm) | Death rate (%) After 1 days | Death rate (%) After 5 days |
|---|---|---|---|---|
| Compound 19 | + buprofezin | 100 + 0.3 | 15 | 75 |
| | + pymetrozin | 100 + 100 | 20 | 85 |
| | + silafluofen | 100 + 1 | 95 | 100 |
| | + imidacloprid | 100 + 0.1 | 85 | 100 |
| Compound 20 | + buprofezin | 100 + 0.3 | 10 | 80 |
| | + pymetrozin | 100 + 100 | 25 | 90 |
| | + silafluofen | 100 + 1 | 85 | 90 |
| | + imidacloprid | 100 + 0.1 | 65 | 95 |
| Compound 39 | + buprofezin | 100 + 0.3 | 15 | 70 |
| | + pymetrozin | 100 + 100 | 30 | 85 |
| | + silafluofen | 100 + 1 | 85 | 85 |
| | + imidacloprid | 100 + 0.1 | 65 | 95 |
| Compound 40 | + buprofezin | 100 + 0.3 | 20 | 75 |
| | + pymetrozin | 100 + 100 | 25 | 90 |
| | + silafluofen | 100 + 1 | 90 | 95 |
| | + imidacloprid | 100 + 0.1 | 75 | 95 |
| Compound 41 | + buprofezin | 100 + 0.3 | 15 | 100 |
| | + pymetrozin | 100 + 100 | 30 | 90 |
| | + silafluofen | 100 + 1 | 85 | 95 |
| | + imidacloprid | 100 + 0.1 | 85 | 100 |
| Compound 42 | + buprofezin | 100 + 0.3 | 25 | 100 |
| | + pymetrozin | 100 + 100 | 35 | 95 |
| | + silafluofen | 100 + 1 | 85 | 95 |
| | + imidacloprid | 100 + 0.1 | 90 | 100 |
| Compound 43 | + buprofezin | 100 + 0.3 | 30 | 100 |
| | + pymetrozin | 100 + 100 | 40 | 95 |

TABLE 4-continued

| Test agent | | Concentration (ppm) | Death rate (%) After 1 days | Death rate (%) After 5 days |
|---|---|---|---|---|
| | + silafluofen | 100 + 1 | 90 | 100 |
| | + imidacloprid | 100 + 0.1 | 90 | 100 |
| Compound 44 | + buprofezin | 100 + 0.3 | 15 | 95 |
| | + pymetrozin | 100 + 100 | 25 | 95 |
| | + silafluofen | 100 + 1 | 75 | 80 |
| | + imidacloprid | 100 + 0.1 | 80 | 95 |
| Compound 45 | + buprofezin | 100 + 0.3 | 20 | 95 |
| | + pymetrozin | 100 + 100 | 30 | 100 |
| | + silafluofen | 100 + 1 | 80 | 80 |
| | + imidacloprid | 100 + 0.1 | 85 | 90 |
| Compound 46 | + buprofezin | 100 + 0.3 | 15 | 80 |
| | + pymetrozin | 100 + 100 | 25 | 90 |
| | + silafluofen | 100 + 1 | 75 | 75 |
| | + imidacloprid | 100 + 0.1 | 70 | 75 |
| Compound 47 | + buprofezin | 100 + 0.3 | 20 | 75 |
| | + pymetrozin | 100 + 100 | 30 | 85 |
| | + silafluofen | 100 + 1 | 65 | 70 |
| | + imidacloprid | 100 + 0.1 | 70 | 85 |
| Compound 48 | + buprofezin | 100 + 0.3 | 25 | 85 |
| | + pymetrozin | 100 + 100 | 35 | 90 |
| | + silafluofen | 100 + 1 | 70 | 75 |
| | + imidacloprid | 100 + 0.1 | 75 | 80 |
| Compound 54 | + buprofezin | 100 + 0.3 | 15 | 75 |
| | + pymetrozin | 100 + 100 | 30 | 75 |
| | + silafluofen | 100 + 1 | 65 | 65 |
| | + imidacloprid | 100 + 0.1 | 80 | 88 |
| Compound 129 | + buprofezin | 100 + 0.3 | 15 | 80 |
| | + pymetrozin | 100 + 100 | 15 | 90 |
| | + silafluofen | 100 + 1 | 90 | 100 |
| | + imidacloprid | 100 + 0.1 | 85 | 100 |
| Compound 130 | + buprofezin | 100 + 0.3 | 20 | 85 |
| | + pymetrozin | 100 + 100 | 25 | 90 |
| | + silafluofen | 100 + 1 | 90 | 95 |
| | + imidacloprid | 100 + 0.1 | 90 | 95 |
| Compound 131 | + buprofezin | 100 + 0.3 | 25 | 85 |
| | + pymetrozin | 100 + 100 | 20 | 85 |
| | + silafluofen | 100 + 1 | 95 | 100 |
| | + imidacloprid | 100 + 0.1 | 85 | 100 |
| Compound 19 | | 100 | 0 | 0 |
| Compound 20 | | 100 | 0 | 0 |
| Compound 39 | | 100 | 0 | 0 |
| Compound 40 | | 100 | 0 | 0 |
| Compound 41 | | 100 | 0 | 0 |
| Compound 42 | | 100 | 0 | 0 |
| Compound 43 | | 100 | 0 | 0 |
| Compound 44 | | 100 | 0 | 0 |
| Compound 45 | | 100 | 0 | 0 |
| Compound 46 | | 100 | 0 | 0 |
| Compound 47 | | 100 | 0 | 0 |
| Compound 48 | | 100 | 0 | 0 |
| Compound 54 | | 100 | 0 | 0 |
| Compound 129 | | 100 | 0 | 0 |
| Compound 130 | | 100 | 0 | 0 |
| Compound 131 | | 100 | 0 | 0 |
| | buprofezin | 0.3 | 0 | 45 |
| | pymetrozin | 100 | 10 | 40 |
| | silafluofen | 1 | 30 | 30 |
| | imidacloprid | 0.1 | 35 | 35 |
| Untreated plot | | — | 0 | 5 |

Test Example 4

Insecticidal Test on Resistant Strain of Two-spotted Spider Mite

A plastic-made cup having a diameter of 8 cm was filled with water and covered with a lid having a hole having a diameter of 1 cm. A notched filter paper was placed over the lid, and a part of the filter paper was hung down from the lid into the water to maintain the filter paper always in a wet state by the capillary phenomenon.

A leaf disk prepared from the first leaves of kidney bean (variety: Topcrop) was placed on the filter paper, and inoculated with 10 female adults of resistant strain of two-spotted spider mite. On a turn table, 50 ml of an agent solution diluted to a predetermined concentration was uniformly sprayed. After the spraying treatment, the whole was left to stand in a thermostatted chamber at 25° C.

Two days after the spraying treatment, the number of alive spider mites were counted, based on which the spider mites death rate were calculated. The test was carried out with two replications of 10 adults. The results are shown in Table 5.

TABLE 5

| Test agent | | Concentration (ppm) | Death rate (%) |
|---|---|---|---|
| Compound 19 | + tebufenpyrad | 100 + 100 | 95 |
|  | + fenbutatin oxide | 100 + 100 | 90 |
|  | + halfenprox | 100 + 100 | 85 |
| Compound 20 | + tebufenpyrad | 100 + 100 | 90 |
|  | + fenbutatin oxide | 100 + 100 | 85 |
|  | + halfenprox | 100 + 100 | 90 |
| Compound 39 | + tebufenpyrad | 100 + 100 | 85 |
|  | + fenbutatin oxide | 100 + 100 | 75 |
|  | + halfenprox | 100 + 100 | 90 |
| Compound 40 | + tebufenpyrad | 100 + 100 | 85 |
|  | + fenbutatin oxide | 100 + 100 | 90 |
|  | + halfenprox | 100 + 100 | 95 |
| Compound 41 | + tebufenpyrad | 100 + 100 | 90 |
|  | + fenbutatin oxide | 100 + 100 | 95 |
|  | + halfenprox | 100 + 100 | 85 |
| Compound 42 | + tebufenpyrad | 100 + 100 | 95 |
|  | + fenbutatin oxide | 100 + 100 | 90 |
|  | + halfenprox | 100 + 100 | 90 |
| Compound 43 | + tebufenpyrad | 100 + 100 | 95 |
|  | + fenbutatin oxide | 100 + 100 | 90 |
|  | + halfenprox | 100 + 100 | 95 |
| Compound 44 | + tebufenpyrad | 100 + 100 | 85 |
|  | + fenbutatin oxide | 100 + 100 | 95 |
|  | + halfenprox | 100 + 100 | 90 |
| Compound 45 | + tebufenpyrad | 100 + 100 | 75 |
|  | + fenbutatin oxide | 100 + 100 | 80 |
|  | + halfenprox | 100 + 100 | 75 |
| Compound 46 | + tebufenpyrad | 100 + 100 | 95 |
|  | + fenbutatin oxide | 100 + 100 | 90 |
|  | + halfenprox | 100 + 100 | 80 |
| Compound 47 | + tebufenpyrad | 100 + 100 | 85 |
|  | + fenbutatin oxide | 100 + 100 | 85 |
|  | + halfenprox | 100 + 100 | 75 |
| Compound 48 | + tebufenpyrad | 100 + 100 | 90 |
|  | + fenbutatin oxide | 100 + 100 | 85 |
|  | + halfenprox | 100 + 100 | 95 |
| Compound 54 | + tebufenpyrad | 100 + 100 | 80 |
|  | + fenbutatin oxide | 100 + 100 | 85 |
|  | + halfenprox | 100 + 100 | 90 |
| Compound 129 | + tebufenpyrad | 100 + 100 | 95 |
|  | + fenbutatin oxide | 100 + 100 | 85 |
|  | + halfenprox | 100 + 100 | 85 |
|  | + spirodiclofen | 100 + 10 | 90 |
| Compound 130 | + tebufenpyrad | 100 + 100 | 90 |
|  | + fenbutatin oxide | 100 + 100 | 95 |
|  | + halfenprox | 100 + 100 | 80 |
|  | + spirodiclofen | 100 + 10 | 75 |
| Compound 131 | + tebufenpyrad | 100 + 100 | 95 |
|  | + fenbutatin oxide | 100 + 100 | 85 |
|  | + halfenprox | 100 + 100 | 90 |
|  | + spirodiclofen | 100 + 10 | 85 |
| Compound 19 |  | 100 | 0 |
| Compound 20 |  | 100 | 0 |
| Compound 39 |  | 100 | 0 |
| Compound 40 |  | 100 | 0 |
| Compound 41 |  | 100 | 0 |
| Compound 42 |  | 100 | 0 |
| Compound 43 |  | 100 | 0 |
| Compound 44 |  | 100 | 0 |
| Compound 45 |  | 100 | 0 |
| Compound 46 |  | 100 | 0 |
| Compound 47 |  | 100 | 0 |
| Compound 48 |  | 100 | 0 |
| Compound 54 |  | 100 | 0 |
| Compound 129 |  | 100 | 5 |
| Compound 130 |  | 100 | 10 |
| Compound 131 |  | 100 | 5 |
| tebufenpyrad |  | 100 | 60 |
| fenbutatin oxide |  | 100 | 50 |
| halfenprox |  | 100 | 35 |
| Untreated plot |  | — | 0 |

Test Example 5

Test for the Effect on Southern Root-knot Nematode (*Meloidogyne Incognita*)

Two kilograms of a soil polluted with southern root-knot nematode was blended with a predetermined dose of a granular preparation. The mixture was filled into a 1/5,000 are Wagner pot. After sowing melon seeds and carrying out the treatment of the present invention, the pot was left to stand in a greenhouse. Sixty days after the treatment, 25 g of the soil was sampled out, the nematode was separated therefrom according to the method of Berman, and the numbers of nematodes were counted after 48 hours. The test was carried out with two replications, on one pot/group.

The results are shown in Table 6. In the tables, "ai" means active ingredient.

TABLE 6

| Test agent | | Dosage (g ai/10a) | Number of nematodes per 25 g of soil sample |
|---|---|---|---|
| Compound 19 | + oxamyl | 300 + 300 | 3 |
|  | + fosthiazate | 300 + 300 | 1 |
| Compound 20 | + oxamyl | 300 + 300 | 4 |
|  | + fosthiazate | 300 + 300 | 2 |
| Compound 39 | + oxamyl | 300 + 300 | 5 |
|  | + fosthiazate | 300 + 300 | 1 |
| Compound 40 | + oxamyl | 300 + 300 | 4 |
|  | + fosthiazate | 300 + 300 | 3 |
| Compound 41 | + oxamyl | 300 + 300 | 3 |
|  | + fosthiazate | 300 + 300 | 2 |
| Compound 42 | + oxamyl | 300 + 300 | 7 |
|  | + fosthiazate | 300 + 300 | 5 |
| Compound 43 | + oxamyl | 300 + 300 | 6 |
|  | + fosthiazate | 300 + 300 | 2 |
| Compound 44 | + oxamyl | 300 + 300 | 5 |
|  | + fosthiazate | 300 + 300 | 5 |
| Compound 45 | + oxamyl | 300 + 300 | 4 |
|  | + fosthiazate | 300 + 300 | 2 |
| Compound 46 | + oxamyl | 300 + 300 | 1 |
|  | + fosthiazate | 300 + 300 | 3 |
| Compound 47 | + oxamyl | 300 + 300 | 5 |
|  | + fosthiazate | 300 + 300 | 3 |
| Compound 48 | + oxamyl | 300 + 300 | 4 |
|  | + fosthiazate | 300 + 300 | 2 |
| Compound 54 | + oxamyl | 300 + 300 | 4 |
|  | + fosthiazate | 300 + 300 | 2 |
| Compound 129 | + oxamyl | 300 + 300 | 8 |
|  | + fosthiazate | 300 + 300 | 2 |

TABLE 6-continued

| Test agent | | Dosage (g ai/10a) | Number of nematodes per 25 g of soil sample |
|---|---|---|---|
| Compound 130 | + oxamyl | 300 + 300 | 5 |
|  | + fosthiazate | 300 + 300 | 1 |
| Compound 131 | + oxamyl | 300 + 300 | 6 |
|  | + fosthiazate | 300 + 300 | 3 |
| Compound 19 | | 300 | 36 |
| Compound 20 | | 300 | 28 |
| Compound 39 | | 300 | 34 |
| Compound 40 | | 300 | 33 |
| Compound 41 | | 300 | 31 |
| Compound 42 | | 300 | 28 |
| Compound 43 | | 300 | 36 |
| Compound 44 | | 300 | 29 |
| Compound 45 | | 300 | 30 |
| Compound 46 | | 300 | 36 |
| Compound 47 | | 300 | 27 |
| Compound 48 | | 300 | 33 |
| Compound 54 | | 300 | 32 |
| Compound 129 | | 300 | 45 |
| Compound 130 | | 300 | 40 |
| Compound 131 | | 300 | 41 |
| oxamyl | | 300 | 13 |
| fosthiazate | | 300 | 7 |
| Untreated group | | — | 33 |

Test Example 6

Test for the Control of Rice Water Weevil (*Lissorhoptrus Oryzophilus*) and Rice Blast on Paddyfield Rice Plant by Nursery Box Application Fifty grams of a granular preparation was applied to rice plant (variety: Koshihikari) cultured in a nursery box. On the same day as the day of treatment (in the middle ten days of May), the rice plant was transplanted to the main paddy field. The controlling effect against rice water weevil was evaluated by investigating the number of hills classified by the extent of injury, on 100 hills in each plot, 21 days after the transplantation, and calculating the overall extent of injury therefrom. The controlling effect against rice blast was evaluated by investigating the areal rate of disease spot 60 days after the transplantation.

Extent of injury=$\{(4A+3B+2C+D)/(4\times N)\}\times 100$ wherein
A: percentage of injured leaves: 91% or higher
B: percentage of injured leaves: 61-90%
C: percentage of injured leaves: 31-60%
D: percentage of injured leaves: 1-30%
N: Number of hills investigated
The results are shown in Table 7.

TABLE 7

| Test agent | | Dosage (g ai/Box) | Extent of injury After 21 days | Areal rate of disease spot (%) After 60 days |
|---|---|---|---|---|
| Compound 19 | +imidacloprid +carpropamid | 0.5 + 1 + 2 | 3.5 | 0.4 |
| Compound 20 | +imidacloprid +carpropamid | 0.5 + 1 + 2 | 2.3 | 0.3 |
| Compound 39 | +imidacloprid +carpropamid | 0.5 + 1 + 2 | 1.5 | 0.1 |
| Compound 40 | +imidacloprid +carpropamid | 0.5 + 1 + 2 | 2.5 | 0.6 |
| Compound 41 | +imidacloprid +carpropamid | 0.5 + 1 + 2 | 1.3 | 0.2 |
| Compound 42 | +imidacloprid +carpropamid | 0.5 + 1 + 2 | 2.5 | 0.2 |
| Compound 43 | +imidacloprid +carpropamid | 0.5 + 1 + 2 | 1.3 | 0.1 |
| Compound 44 | +imidacloprid +carpropamid | 0.5 + 1 + 2 | 3.8 | 0.4 |
| Compound 45 | +imidacloprid +carpropamid | 0.5 + 1 + 2 | 2.2 | 0.3 |
| Compound 46 | +imidacloprid +carpropamid | 0.5 + 1 + 2 | 1.8 | 0.4 |
| Compound 47 | +imidacloprid +carpropamid | 0.5 + 1 + 2 | 2.8 | 0.2 |
| Compound 48 | +imidacloprid +carpropamid | 0.5 + 1 + 2 | 1.9 | 0.5 |
| Compound 54 | +imidacloprid +carpropamid | 0.5 + 1 + 2 | 1.3 | 0.6 |
| Compound 129 | +imidacloprid +carpropamid | 0.5 + 1 + 2 | 3.5 | 0.5 |
| Compound 130 | +imidacloprid +carpropamid | 0.5 + 1 + 2 | 2.9 | 0.4 |
| Compound 131 | +imidacloprid +carpropamid | 0.5 + 1 + 2 | 3.2 | 0.3 |
| Compound 19 | | 0.5 | 38.9 | 8.3 |
| Compound 20 | | 0.5 | 37.4 | 8.1 |
| Compound 39 | | 0.5 | 38.9 | 8.2 |
| Compound 40 | | 0.5 | 39.0 | 7.9 |
| Compound 41 | | 0.5 | 43.2 | 8.5 |
| Compound 42 | | 0.5 | 39.5 | 8.3 |
| Compound 43 | | 0.5 | 44.3 | 8.9 |
| Compound 44 | | 0.5 | 45.9 | 9.1 |
| Compound 45 | | 0.5 | 38.8 | 8.2 |
| Compound 46 | | 0.5 | 42.7 | 8.5 |
| Compound 47 | | 0.5 | 40.9 | 7.8 |
| Compound 48 | | 0.5 | 39.8 | 7.4 |
| Compound 54 | | 0.5 | 41.7 | 9.0 |
| Compound 129 | | 0.5 | 40.3 | 9.1 |
| Compound 130 | | 0.5 | 39.0 | 8.3 |
| Compound 131 | | 0.5 | 41.2 | 8.3 |
| imidacloprid | +carpropamid | 1 + 2 | 5.8 | 1.2 |
| Untreated plot | | — | 45.6 | 8.2 |

Test Example 7

Test for the Control of Small Brown Planthopper (*Laodelphax Striatellus*) and Rice Leafroller (*Cnaphalocrosis Medinalis*) on Paddyfield Rice Plant by Nursery Box Application Fifty grams of a granular preparation was applied to rice plant (variety: Nihombare) cultured in a nursery box, after which the rice plant was transplanted to the main paddy field (in the middle of May). The controlling effect against small brown planthopper was evaluated by investigating the number of parasitic insects on 30 hills per each plot, 40 days and 60 days after the transplantation. The controlling effect against rice leafroller was evaluated by investigating the number of injured leaves on 100 hills per each plot, 50 days after the transplantation.

The results are shown in Table 8.

TABLE 8

| Test agent | | Dosage (g ai/Box) | Number of parasitic planthoppers per 30 hills | | Percentage of injured leaves (%) |
|---|---|---|---|---|---|
| | | | After 40 days | After 60 days | After 50 days |
| Compound 19 | +imidacloprid | 0.5 + 1 | 0 | 4 | 0.03 |
| | +benfuracarb | 0.5 + 2.5 | 17 | 48 | 0.07 |
| Compound 20 | +imidacloprid | 0.5 + 1 | 0 | 7 | 0.05 |
| | +benfuracarb | 0.5 + 2.5 | 22 | 55 | 0.08 |
| Compound 39 | +imidacloprid | 0.5 + 1 | 0 | 9 | 0.04 |
| | +benfuracarb | 0.5 + 2.5 | 24 | 45 | 0.07 |
| Compound 40 | +imidacloprid | 0.5 + 1 | 0 | 10 | 0.02 |
| | +benfuracarb | 0.5 + 2.5 | 17 | 54 | 0.08 |
| Compound 41 | +imidacloprid | 0.5 + 1 | 0 | 6 | 0.04 |
| | +benfuracarb | 0.5 + 2.5 | 33 | 34 | 0.06 |
| Compound 42 | +imidacloprid | 0.5 + 1 | 0 | 7 | 0.03 |
| | +benfuracarb | 0.5 + 2.5 | 31 | 65 | 0.08 |
| Compound 43 | +imidacloprid | 0.5 + 1 | 0 | 9 | 0.02 |
| | +benfuracarb | 0.5 + 2.5 | 14 | 33 | 0.06 |
| Compound 44 | +imidacloprid | 0.5 + 1 | 0 | 3 | 0.03 |
| | +benfuracarb | 0.5 + 2.5 | 18 | 53 | 0.08 |
| Compound 45 | +imidacloprid | 0.5 + 1 | 0 | 4 | 0.02 |
| | +benfuracarb | 0.5 + 2.5 | 25 | 23 | 0.08 |
| Compound 46 | +imidacloprid | 0.5 + 1 | 0 | 7 | 0.05 |
| | +benfuracarb | 0.5 + 2.5 | 13 | 54 | 0.09 |
| Compound 47 | +imidacloprid | 0.5 + 1 | 0 | 7 | 0.04 |
| | +benfuracarb | 0.5 + 2.5 | 16 | 36 | 0.08 |
| Compound 48 | +imidacloprid | 0.5 + 1 | 0 | 6 | 0.03 |
| | +benfuracarb | 0.5 + 2.5 | 33 | 28 | 0.08 |
| Compound 54 | +imidacloprid | 0.5 + 1 | 0 | 9 | 0.02 |
| | +benfuracarb | 0.5 + 2.5 | 31 | 45 | 0.07 |
| Compound 129 | +imidacloprid | 0.5 + 1 | 0 | 7 | 0.04 |
| | +benfuracarb | 0.5 + 2.5 | 15 | 57 | 0.08 |
| Compound 130 | +imidacloprid | 0.5 + 1 | 0 | 6 | 0.06 |
| | +benfuracarb | 0.5 + 2.5 | 18 | 61 | 0.09 |
| Compound 131 | +imidacloprid | 0.5 + 1 | 0 | 8 | 0.05 |
| | +benfuracarb | 0.5 + 2.5 | 20 | 49 | 0.08 |
| Compound 19 | | 0.5 | 325 | 389 | 0.16 |
| Compound 20 | | 0.5 | 315 | 354 | 0.15 |
| Compound 39 | | 0.5 | 343 | 372 | 0.25 |
| Compound 40 | | 0.5 | 322 | 358 | 0.33 |
| Compound 41 | | 0.5 | 333 | 385 | 0.35 |
| Compound 42 | | 0.5 | 345 | 389 | 0.22 |
| Compound 43 | | 0.5 | 309 | 334 | 0.17 |
| Compound 44 | | 0.5 | 323 | 358 | 0.24 |
| Compound 45 | | 0.5 | 353 | 395 | 0.13 |
| Compound 46 | | 0.5 | 349 | 387 | 0.18 |
| Compound 47 | | 0.5 | 328 | 365 | 0.11 |
| Compound 48 | | 0.5 | 345 | 383 | 0.33 |
| Compound 54 | | 0.5 | 328 | 334 | 0.25 |
| Compound 129 | | 0.5 | 323 | 390 | 0.13 |
| Compound 130 | | 0.5 | 331 | 382 | 0.16 |
| Compound 131 | | 0.5 | 342 | 391 | 0.14 |
| imidacloprid | | 1 | 0 | 29 | 1.63 |
| benfuracarb | | 2.5 | 78 | 244 | 1.13 |
| Untreated plot | | — | 355 | 388 | 1.54 |

Test Example 8

Test for the Control of Diamondback Moth (*Plutella Xyloxtella*) and Aphid on Cabbage by Soil Treatment A granular preparation was mixed into bed soil, and the mixture was filled into a cell seedling box and sown with seeds of cabbage (variety: YR Seitoku). Otherwise, cell seedling planted cabbage was treated with the granular agent either by a treatment in the foliage leaf extraction period, or by a pretransplanting treatment, or by a pricking-in hole treatment, or by a plant foot treatment after the planting. Twenty one days after the transplanting (in the middle of June), the number of parasitic insects was counted on 30 hills in the case of diamondback moth and on 10 hills in the case of aphid.

The results are shown in Table 9.

| Test agent | | Dosage (mg ai/hill) | Method of treatment | Number of parasitic insects per 30 hills | |
|---|---|---|---|---|---|
| | | | | Diamond-back moth | Aphid |
| Compound 19 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 20 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 39 | +imidacloprid | 5 + 20 | pre-transplanting treatment | 0 | 0 |
| | | 5 + 20 | pricking-in hole treatment | 0 | 0 |

-continued

| Test agent | | Dosage (mg ai/hill) | Method of treatment | Number of parasitic insects per 30 hills | |
|---|---|---|---|---|---|
| | | | | Diamond-back moth | Aphid |
| | | 5 + 20 | plant foot treatment | 0 | 0 |
| Compound 40 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 41 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 42 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 43 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 44 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 45 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 46 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 47 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 48 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 54 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |

-continued

| Test agent | | Dosage (mg ai/hill) | Method of treatment | Number of parasitic insects per 30 hills | |
|---|---|---|---|---|---|
| | | | | Diamond-back moth | Aphid |
| Compound 129 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 130 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 131 | +imidacloprid | 5 + 20 | pre-transplanting treatment | 0 | 0 |
| | | 5 + 20 | pricking-in hole treatment | 0 | 0 |
| | | 5 + 20 | plant foot treatment | 0 | 0 |
| Compound 19 | | 5 | soil incorporation | 1 | 445 |
| | | 5 | true leaf extraction season treatment | 2 | 457 |
| | | 5 | pre-transplanting treatment | 1 | 399 |
| | | 5 | pricking-in hole treatment | 1 | 467 |
| | | 5 | plant foot treatment | 2 | 489 |
| Compound 20 | | 5 | soil incorporation | 4 | 512 |
| | | 5 | true leaf extraction season treatment | 2 | 498 |
| | | 5 | pre-transplanting treatment | 6 | 478 |
| | | 5 | pricking-in hole treatment | 3 | 499 |
| | | 5 | plant foot treatment | 5 | 501 |
| Compound 39 | | 5 | soil incorporation | 3 | 513 |
| | | 5 | true leaf extraction season treatment | 2 | 487 |
| | | 5 | pre-transplanting treatment | 4 | 457 |
| | | 5 | pricking-in hole treatment | 3 | 437 |
| | | 5 | plant foot treatment | 2 | 456 |
| Compound 40 | | 5 | soil incorporation | 2 | 472 |
| | | 5 | true leaf extraction season treatment | 1 | 510 |
| | | 5 | pre-transplanting treatment | 1 | 477 |
| | | 5 | pricking-in hole treatment | 1 | 486 |

-continued

| Test agent | Dosage (mg ai/hill) | Method of treatment | Number of parasitic insects per 30 hills | |
|---|---|---|---|---|
| | | | Diamond-back moth | Aphid |
| | 5 | plant foot treatment | 3 | 478 |
| Compound 41 | 5 | soil incorporation | 3 | 457 |
| | 5 | true leaf extraction season treatment | 2 | 495 |
| | 5 | pre-transplanting treatment | 1 | 458 |
| | 5 | pricking-in hole treatment | 2 | 511 |
| | 5 | plant foot treatment | 2 | 456 |
| Compound 42 | 5 | soil incorporation | 3 | 475 |
| | 5 | true leaf extraction season treatment | 2 | 485 |
| | 5 | pre-transplanting treatment | 3 | 435 |
| | 5 | pricking-in hole treatment | 1 | 473 |
| | 5 | plant foot treatment | 3 | 498 |
| Compound 43 | 5 | soil incorporation | 2 | 501 |
| | 5 | true leaf extraction season treatment | 2 | 448 |
| | 5 | pre-transplanting treatment | 3 | 482 |
| | 5 | pricking-in hole treatment | 1 | 447 |
| | 5 | plant foot treatment | 2 | 467 |
| Compound 44 | 5 | soil incorporation | 3 | 449 |
| | 5 | true leaf extraction season treatment | 2 | 502 |
| | 5 | pre-transplanting treatment | 3 | 498 |
| | 5 | pricking-in hole treatment | 3 | 478 |
| | 5 | plant foot treatment | 2 | 492 |
| Compound 45 | 5 | soil incorporation | 2 | 472 |
| | 5 | true leaf extraction season treatment | 2 | 463 |
| | 5 | pre-transplanting treatment | 1 | 472 |
| | 5 | pricking-in hole treatment | 5 | 465 |
| | 5 | plant foot treatment | 4 | 489 |
| Compound 46 | 5 | soil incorporation | 1 | 505 |
| | 5 | true leaf extraction season | 3 | 498 |

| Test agent | Dosage (mg ai/hill) | Method of treatment | Number of parasitic insects per 30 hills | |
|---|---|---|---|---|
| | | | Diamond-back moth | Aphid |
| | 5 | treatment pre-transplanting treatment | 1 | 479 |
| | 5 | pricking-in hole treatment | 3 | 447 |
| | 5 | plant foot treatment | 2 | 469 |
| Compound 47 | 5 | soil incorporation | 3 | 438 |
| | 5 | true leaf extraction season treatment | 2 | 499 |
| | 5 | pre-transplanting treatment | 4 | 452 |
| | 5 | pricking-in hole treatment | 1 | 477 |
| | 5 | plant foot treatment | 2 | 511 |
| Compound 48 | 5 | soil incorporation | 5 | 502 |
| | 5 | true leaf extraction season treatment | 2 | 442 |
| | 5 | pre-transplanting treatment | 5 | 476 |
| | 5 | pricking-in hole treatment | 1 | 492 |
| | 5 | plant foot treatment | 4 | 456 |
| Compound 54 | 5 | soil incorporation | 1 | 478 |
| | 5 | true leaf extraction season treatment | 3 | 459 |
| | 5 | pre-transplanting treatment | 1 | 487 |
| | 5 | pricking-in hole treatment | 3 | 499 |
| | 5 | plant foot treatment | 2 | 463 |
| Compound 129 | 5 | soil incorporation | 2 | 455 |
| | 5 | true leaf extraction season treatment | 1 | 458 |
| | 5 | pre-transplanting treatment | 2 | 402 |
| | 5 | pricking-in hole treatment | 3 | 397 |
| | 5 | plant foot treatment | 1 | 481 |
| Compound 130 | 5 | soil incorporation | 1 | 453 |
| | 5 | true leaf extraction season treatment | 1 | 399 |
| | 5 | pre-transplanting treatment | 1 | 421 |
| | 5 | pricking-in hole treatment | 2 | 467 |

-continued

| Test agent | Dosage (mg ai/hill) | Method of treatment | Number of parasitic insects per 30 hills | |
|---|---|---|---|---|
| | | | Diamond-back moth | Aphid |
| | 5 | plant foot treatment | 1 | 498 |
| Compound 131 | 5 | soil incorporation | 1 | 432 |
| | 5 | true leaf extraction season treatment | 1 | 465 |
| | 5 | pre-transplanting treatment | 2 | 428 |
| | 5 | pricking-in hole treatment | 2 | 391 |
| | 5 | plant foot treatment | 1 | 486 |
| imidacloprid | 20 | pre-transplanting treatment | 35 | 10 |
| | 20 | picking-in hole treatment | 40 | 16 |
| | 20 | plant foot treatment | 38 | 13 |
| Untreated plot | — | | 41 | 479 |

Note:
The effect in soil incorporation and true leaf extraction season treatment could not be evaluated due to phytotoxicity, in cases of a single use of imidacloprid and a mixed use of imidacloprid.

Test Example 9

Test for the Effect Against Cutworm on Beet

Beet seedlings (variety: Monoace S) planted in a paper pot was treated with 3 L m² of a solution of an agent diluted to a predetermined concentration, by the method of drench. Just after the drench, the plant was set. Predetermined days after the setting, the number of injured hills per 100 hills was counted. The test was carried out with two replications, 80 m² per one plot.

The results are shown in Table 10.

TABLE 10

| Test agent | Dosage (g ai/10a) | Number of injured hills per 100 hills | | |
|---|---|---|---|---|
| | | After 60 days | After 90 days | After 120 days |
| Compound 19 + acephate | 15 + 50 | 0 | 3 | 11 |
| Compound 20 + acephate | 15 + 50 | 0 | 4 | 10 |
| Compound 39 + acephate | 15 + 50 | 0 | 2 | 8 |
| Compound 40 + acephate | 15 + 50 | 0 | 1 | 7 |
| Compound 41 + acephate | 15 + 50 | 0 | 5 | 9 |
| Compound 42 + acephate | 15 + 50 | 0 | 4 | 10 |
| Compound 43 + acephate | 15 + 50 | 0 | 2 | 6 |
| Compound 44 + acephate | 15 + 50 | 0 | 3 | 8 |
| Compound 45 + acephate | 15 + 50 | 0 | 1 | 5 |
| Compound 46 + acephate | 15 + 50 | 0 | 4 | 11 |
| Compound 47 + acephate | 15 + 50 | 0 | 5 | 12 |
| Compound 48 + acephate | 15 + 50 | 0 | 2 | 5 |
| Compound 54 + acephate | 15 + 50 | 0 | 2 | 6 |
| Compound 129 + acephate | 15 + 50 | 0 | 3 | 14 |
| Compound 130 + acephate | 15 + 50 | 0 | 2 | 9 |
| Compound 131 + acephate | 15 + 50 | 0 | 5 | 12 |
| Compound 19 | 15 | 0 | 8 | 21 |
| Compound 20 | 15 | 0 | 7 | 20 |
| Compound 39 | 15 | 0 | 6 | 17 |
| Compound 40 | 15 | 0 | 9 | 23 |
| Compound 41 | 15 | 0 | 7 | 21 |
| Compound 42 | 15 | 0 | 8 | 22 |
| Compound 43 | 15 | 0 | 6 | 19 |
| Compound 44 | 15 | 0 | 7 | 20 |
| Compound 45 | 15 | 0 | 9 | 23 |
| Compound 46 | 15 | 0 | 8 | 20 |
| Compound 47 | 15 | 0 | 9 | 21 |
| Compound 48 | 15 | 0 | 7 | 18 |
| Compound 54 | 15 | 0 | 8 | 19 |
| Compound 129 | 15 | 0 | 10 | 22 |
| Compound 130 | 15 | 0 | 7 | 19 |
| Compound 131 | 15 | 0 | 8 | 21 |
| acephate | 50 | 2 | 14 | 24 |
| Untreated plot | — | 6 | 26 | 30 |

Test Example 10

Test for the Control of Citrus Yellow Thrips (*Frankliniella Occidentalis*) on Egg Plant by the Combined Use with Natural Enemy Pesticide An agent solution diluted to a predetermined concentration was sprayed by means of a shouldered spraying machine to citrus yellow thrips (Frankliniella occidentalis) parasitic on egg-plant (variety: Senryo No. 2) in a vinyl house. After air-dryness, 100 heads per hill of *Amblyseius cucumeris* were let inoculate. Fourteen days, twenty one days and twenty eight days after the treatment, the numbers of citrus yellow thrips and *Amblyseius cucumeris* were counted on twenty leaves showing a most serious injury (the first ten days of June).

The results are shown in Table 11.

TABLE 11

| Test agent | Amount applied (ppm or adults number) | Number of parasitic insects per 20 leaves | | |
|---|---|---|---|---|
| | | After 14 days | After 21 days | After 28 days |
| Compound 19 + *Amblyseius cucumeris* | 100 ppm + 100 adults/hill | 2 | 0 | 3 |
| Compound 20 + *Amblyseius cucumeris* | 100 ppm + 100 adults/hill | 3 | 0 | 2 |
| Compound 39 + *Amblyseius cucumeris* | 100 ppm + 100 adults/hill | 1 | 0 | 1 |
| Compound 40 + *Amblyseius cucumeris* | 100 ppm + 100 adults/hill | 4 | 0 | 4 |
| Compound 41 + *Amblyseius cucumeris* | 100 ppm + 100 adults/hill | 5 | 1 | 6 |
| Compound 42 + *Amblyseius cucumeris* | 100 ppm + 100 adults/hill | 3 | 0 | 4 |
| Compound 43 + *Amblyseius cucumeris* | 100 ppm + 100 adults/hill | 1 | 0 | 2 |
| Compound 44 + *Amblyseius cucumeris* | 100 ppm + 100 adults/hill | 1 | 0 | 1 |
| Compound 45 + *Amblyseius cucumeris* | 100 ppm + 100 adults/hill | 2 | 0 | 4 |
| Compound 46 + *Amblyseius cucumeris* | 100 ppm + 100 adults/hill | 4 | 1 | 6 |
| Compound 47 + *Amblyseius cucumeris* | 100 ppm + 100 adults/hill | 1 | 0 | 2 |
| Compound 48 + *Amblyseius cucumeris* | 100 ppm + 100 adults/hill | 3 | 1 | 5 |
| Compound 54 + *Amblyseius cucumeris* | 100 ppm + 100 adults/hill | 2 | 0 | 2 |
| Compound 129 + *Amblyseius cucumeris* | 100 ppm + 100 adults/hill | 2 | 0 | 3 |
| Compound 130 + *Amblyseius cucumeris* | 100 ppm + 100 adults/hill | 4 | 0 | 2 |
| Compound 131 + *Amblyseius cucumeris* | 100 ppm + 100 adults/hill | 3 | 0 | 4 |
| Compound 19 | 100 ppm | 20 | 27 | 55 |
| Compound 20 | 100 ppm | 21 | 28 | 49 |
| Compound 39 | 100 ppm | 19 | 32 | 58 |
| Compound 40 | 100 ppm | 22 | 31 | 52 |
| Compound 41 | 100 ppm | 18 | 29 | 59 |
| Compound 42 | 100 ppm | 19 | 25 | 50 |
| Compound 43 | 100 ppm | 23 | 31 | 57 |
| Compound 44 | 100 ppm | 25 | 33 | 53 |
| Compound 45 | 100 ppm | 18 | 29 | 59 |
| Compound 46 | 100 ppm | 20 | 34 | 57 |
| Compound 47 | 100 ppm | 21 | 27 | 52 |
| Compound 48 | 100 ppm | 19 | 31 | 59 |
| Compound 54 | 100 ppm | 18 | 25 | 61 |
| Compound 129 | 100 ppm | 19 | 29 | 51 |
| Compound 130 | 100 ppm | 21 | 28 | 50 |
| Compound 131 | 100 ppm | 23 | 30 | 54 |
| *Amblyseius cucumeris* | 100 adults/hill | 8 | 5 | 15 |
| Untreated plot | — | 22 | 32 | 58 |

Test Example 11

Test for the Control of Rice Leafroller (*Cnaphalocrocis Medinalis*), Rice Blast, Barnyard Grass (*Echinochloa crus-galli*) and Bulrush (*Scirpus Juncoides Roxb.*) on Paddyfield Rice Plant by Submerged Application to Main Paddyfield Ten days after the transplantation (in the middle ten days of May), a granular preparation was applied to water surface of main paddyfield. The controlling effect on rice leafroller was evaluated by counting the injured leaves on each plot (100 hills) 50 days after the transplantation, and calculating the percentage of injured leaves therefrom. The effect against rice blast was evaluated by measuring the areal rate of disease spot 60 days after the transplantation. The effects against barnyard grass and bulrush were evaluated by measuring the herbicidal effect by the naked eye four weeks after the treatment and expressing the result by numerically (0 means "no effect", and 10 means "complete withering"). At the same time, the chemical injury on rice plant was also evaluated (0 means "no influence").

The results are shown in Table 12.

TABLE 12

| Test agent Dosage (g ai/10a) | Percentage of injured leaves (%) After 50 days | Areal rate of disease spot (%) After 60 days | Herbicidal effect | | Phytotoxicity rice |
|---|---|---|---|---|---|
| | | | barnyard grass | fulrush | |
| Compound 129 + pyroquilon + bensulfron-methyl + indanofan 10.0 + 150.0 + 5.0 + 15.0 | 0.13 | 0.5 | 10 | 10 | 0 |
| Compound 129 + fenoxanyl + bensulfron-methyl + indanofan 10.0 + 250.0 + 5.0 + 15.0 | 0.12 | 0.4 | 10 | 10 | 0 |
| Compound 130 + pyroquilon + bensulfron-methyl + indanofan 10.0 + 150.0 + 5.0 + 15.0 | 0.11 | 0.3 | 10 | 10 | 0 |
| Compound 130 + fenoxanyl + bensulfron-methyl + indanofan 10.0 + 250.0 + 5.0 + 15.0 | 0.15 | 0.5 | 10 | 10 | 0 |

TABLE 12-continued

| Test agent Dosage (g ai/10a) | Percentage of injured leaves (%) After 50 days | Areal rate of disease spot (%) After 60 days | Herbicidal effect | | Phyto- toxicity rice |
|---|---|---|---|---|---|
| | | | barnyard grass | fulrush | |
| Compound 131 + pyroquilon + bensulfron-methyl + indanofan 10.0 + 150.0 + 5.0 + 15.0 | 0.13 | 0.3 | 10 | 10 | 0 |
| Compound 131 + fenoxanyl + bensulfron-methyl + indanofan 10.0 + 250.0 + 5.0 + 15.0 | 0.14 | 0.4 | 10 | 10 | 0 |
| Compound 129 10.0 | 0.15 | 8.1 | 0 | 0 | 0 |
| Compound 130 10.0 | 0.13 | 7.9 | 0 | 0 | 0 |
| Compound 131 10.0 | 0.16 | 8.3 | 0 | 0 | 0 |
| pyroquilon + bensulfron-methyl + indanofan 250.0 + 5.0 + 15.0 | 1.56 | 0.6 | 10 | 10 | 0 |
| fenoxanyl + bensulfron-methyl + indanofan 250.0 + 5.0 + 15.0 | 1.63 | 0.8 | 10 | 10 | 0 |
| Untreated plot — | 1.66 | 8.2 | 0 | 0 | 0 |

What is claimed is:

1. A composition for noxious organisms-controlling agent comprising, as active ingredients thereof, one or more phthalamide derivatives represented by formula (I):

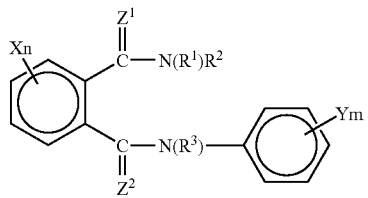

(I)

wherein $R^1$ represents a hydrogen atom, $R^2$ represents a $C_1$-$C_6$ alkyl group, a $C_1$-$C_6$ alkylthio $C_1$-$C_6$ alkyl group, a $C_1$-$C_6$ alkylsulfinyl $C_1$-$C_6$ alkyl group or a $C_1$-$C_6$ alkylsulfonyl $C_1$-$C_6$ alkyl group, $R^3$ represents a hydrogen atom, X represents a halogen atom, n represents 1, each of $Z^1$ and $Z^2$ represents an oxygen atom, Y may be the same or different and represents a halogen atom, a $C_1$-$C_6$ alkyl group, a halo $C_1$-$C_6$ alkyl group or a halo $C_1$-$C_6$ alkoxy group, and m represents 2 or 3; and buprofezin.

2. A composition for noxious organisms-controlling agent according to claim 1, wherein buprofezin is 0.05 to 2,000 parts by weight per part by weight of the phthalamide derivative.

3. A composition for noxious organisms-controlling agent according to claim 1, wherein the phihalamide derivative represented by formula (I) is
$N^2$-(1,1-dimethyl-2-methylthioethyl)-3-iodo-$N^1$-{2-methyl-4-[1,2,2,2-tetrafluoro-1-(trifluoromethyl)-ethyl]phenyl}phthalamide, $N^2$-(1,1-dimethyl-2-methylsulfonylethyl)-3-iodo-$N^1$-{2-methyl-4-[1,2,2,2-tetrafluoro-1-(trifluoromethyl)ethyl]-phenyl}-phthalamide or $N^2$-(1,1-dimethyl-2-methylsulfinylethyl)-3-iodo-$N^1$-{2-methyl-4-[1,2,2,2-tetrafluoro-1-(trifluoromethyl)ethyl]phenyl}phthalamide.

4. A method for using a composition for noxious organisms-controlling agent characterized by treating an objective noxious organism, an objective useful plant, a seed of an objective useful plant, soil or a cultivation carrier of an objective useful plant, with an effective amount of the composition for noxious organisms-controlling agent according to claim 1 for the purpose of protecting an useful plant from a noxious organism.

* * * * *